United States Patent
Engelen et al.

(10) Patent No.: US 12,163,136 B2
(45) Date of Patent: Dec. 10, 2024

(54) BRASSICA PLANT RESISTANT TO PLASMODIOPHORA BRASSICAE (CLUBROOT)

(71) Applicant: BASF Agricultural Solutions Seed US LLC, Florham Park, NJ (US)

(72) Inventors: Steven Engelen, Ghent (BE); Stephen Rae, Ghent (BE); Godfrey Chongo, Saskatoon (CA); Jasper Devlamynck, Deinze (BE); Kim Crommar, Ghent (BE); Katrien Van Audenhove, Ghent (BE)

(73) Assignee: BASF AGRICULTURAL SOLUTIONS SEED US LLC, Florham Park, NJ (US)

( * ) Notice: Subject to any disclaimer, the term of this patent is extended or adjusted under 35 U.S.C. 154(b) by 609 days.

(21) Appl. No.: 16/981,196

(22) PCT Filed: Mar. 15, 2019

(86) PCT No.: PCT/US2019/022601
§ 371 (c)(1),
(2) Date: Sep. 15, 2020

(87) PCT Pub. No.: WO2019/178554
PCT Pub. Date: Sep. 19, 2019

(65) Prior Publication Data
US 2021/0017529 A1    Jan. 21, 2021

(30) Foreign Application Priority Data
Mar. 16, 2018 (EP) ..................... 18162162

(51) Int. Cl.
| | |
|---|---|
| *C12N 15/82* | (2006.01) |
| *A01H 1/00* | (2006.01) |
| *A01H 5/10* | (2018.01) |
| *C12Q 1/68* | (2018.01) |
| *A01H 6/20* | (2018.01) |

(52) U.S. Cl.
CPC ............. *C12N 15/82* (2013.01); *A01H 1/125* (2021.01); *A01H 5/10* (2013.01); *C12Q 1/68* (2013.01); *A01H 6/20* (2018.05)

(58) Field of Classification Search
None
See application file for complete search history.

(56) References Cited

U.S. PATENT DOCUMENTS

| | | | |
|---|---|---|---|
| 5,538,848 A | 7/1996 | Livak et al. | |
| 2005/0142122 A1 | 6/2005 | Diederichsen et al. | |
| 2013/0254929 A1 | 9/2013 | Matsumoto et al. | |
| 2013/0296393 A1 | 11/2013 | Hayashi et al. | |
| 2015/0284740 A1 | 10/2015 | Van Den et al. | |
| 2017/0105380 A1 | 4/2017 | Gingera et al. | |

FOREIGN PATENT DOCUMENTS

| | | |
|---|---|---|
| EP | 1547462 A1 | 6/2005 |
| WO | 2005090578 A1 | 9/2005 |
| WO | 2008101343 A1 | 8/2008 |
| WO | 2011044694 A1 | 4/2011 |
| WO | 2012039445 A1 | 3/2012 |
| WO | 2016176358 A2 | 11/2016 |
| WO | 2017102923 A1 | 6/2017 |

OTHER PUBLICATIONS

Hatakeyama K, Suwabe K, Tomita RN, Kato T, Nunome T, et al. (2013). PLoS One 8(1): e54745. oi:10.1371/journal.pone.0054745.*
Kopec PM, Mikolajczyk K, Jajor E, Perek A, Nowakowska J, Obermeier C, Chawla HS, Korbas M, Bartkowiak-Broda I and Karlowski WM (2021) Front. Plant Sci. 12:639631. doi: 10.3389/fpls.2021.639631.*
Lv et al. Horticulture Research ( 2020) 7:34.*
Višnjevec, et al. "Glucosinolates and isothiocyantes in processed rapeseed determined by HPLC-DAD-qTOF." Plants 10.11 (2021): 2548. (Year: 2021).*
Gehringer, et al. "New oilseed rape (*Brassica napus*) hybrids with high levels of heterosis for seed yield under nutrient-poor conditions." Breeding Science 57.4 (2007): 315-320. (Year: 2007).*
Diederichsen, et al., "Status and Perspectives of Clubroot Resistance Breeding in Crucifer Crops", Journal of Plant Growth Regulation, vol. 28, May 8, 2009, pp. 265-281.
F. M. Humpherson-Jones., "Glasshouse evaluation of fungicides, biocides and surfactants for control of clubroot", Tests of Agrochemicals and Cultivars, vol. 114, 1989, pp. 36-37.
Geoffrey R. Dixon, "Chapter 1—The Occurrence and Economic Impact of Plasmodiophora brassicae and Clubroot Disease", Journal of Plant Growth Regulation, vol. 28, Apr. 22, 2009, pp. 194-202.
Hatakeyama, et al., "Identification and Characterization of Crr1a, a Gene for Resistance to Clubroot Disease (Plasmodiophora brassicae Woronin) in *Brassica rapa* L.", PLOS One, vol. 8, Issue 1, Jan. 30, 2013, pp. e54745 (1-10).
Hwang, et al., "Plasmodiophora brassicae: a review of an emerging pathogen of the Canadian canola (*Brassica napus*) crop", Molecular Plant Pathology, vol. 13, Issue 2, Feb. 2012, pp. 105-113.
Kato, et al., "Fine mapping of the clubroot resistance gene CRb and development of a useful selectable marker in *Brassica rapa*", Breeding Science, vol. 63, 2013, pp. 116-124.
Larkan, et al., "The *Brassica napus* blackleg resistance gene LepR3 encodes a receptor-like protein triggered by the Leptosphaeria maculans effector AVRLM1", New Phytologist, vol. 197, Issue 2, Dec. 3, 2012, pp. 595-605.

(Continued)

*Primary Examiner* — Charles Logsdon
(74) *Attorney, Agent, or Firm* — ArentFox Schiff LLP

(57) ABSTRACT

The present invention relates to clubroot resistance in *Brassica*. More specifically, the invention relates to the CRT clubroot resistance gene, as well as to methods to create clubroot resistant *Brassica* plants.

7 Claims, 14 Drawing Sheets
Specification includes a Sequence Listing.

(56) References Cited

OTHER PUBLICATIONS

Piao, et al., "Genetics of Clubroot Resistance in *Brassica* Species", Journal of Plant Growth Regulation, vol. 28, Apr. 16, 2009, pp. 252-264.

Rice, et al., "EMBOSS: The European Molecular Biology Open Software Suite", The European Molecular Biology Open Software Suite, vol. 16, Issue 6, Jun. 2000, pp. 276-277.

Sakamoto, et al., "Mapping of isolate-specific QTLs for clubroot resistance in Chinese cabbage (*Brassica rapa* L. ssp. *pekinensis*)", Theoretical and Applied Genetics, vol. 117, Jul. 9, 2008, pp. 759-767.

Strelkov, et al., "Characterization of Plasmodiophora brassicae populations from Alberta, Canada", Canadian Journal of Plant Pathology, vol. 28, Issue 3, Sep. 2006, pp. 467-474.

Ueno, et al., "Molecular characterization of the CRa gene conferring clubroot resistance in *Brassica rapa*", Plant Molecular Biology, vol. 80, Oct. 4, 2012, pp. 621-629.

Van Der Biezen, et al., "The NB-ARC domain: a novel signalling motif shared by plant resistance gene products and regulators of cell death in animals", Current Biology, vol. 8, Issue 7, 1998, pp. R226-R228.

Werner, et al., "Genetic mapping of clubroot resistance genes in oilseed rape", Theoretical and Applied Genetics, vol. 116, Article No. 363, Nov. 27, 2007, pp. 30-33.

Wu, et al., "Efficient and Accurate Construction of Genetic Linkage Maps from the Minimum Spanning Tree of a Graph", PLOS Genetics, vol. 4, Issue 10, Oct. 2008, pp. e1000212(1-11).

Xue, et al., Isolation and Variation in Virulence of Single-Spore Isolates of Plasmodiophora brassicae from Canada, Plant Disease, vol. 92, Issue 3, Mar. 2008, pp. 456-462.

Yu, et al., "Genotyping-by-sequencing reveals three QTL for clubroot resistance to six pathotypes of Plasmodiophora prassicae in *Brassica rapa*", Scientific Reports, vol. 7, No. 4516, Jul. 3, 2017, pp. 1-11.

"*Brassica rapa* subsp, pekinensis isolate BrTNL3 disease resistance protein gene, complete cds", Database EMBL [Online], retrieved from EBI Database accession No. FJ842820, XP002804979, Nov. 25, 2009, 2 pages.

European Search Report for EP Patent Application No. 19766541.7, Issued on Jan. 10, 2022, 2 pages.

International Search Report issued in PCT/US2019/022601, dated Jun. 27, 2019, pp. 1-3.

* cited by examiner

```
SEQ ID NO: 2    1  atgctctctcattagctctcttcctcttgtcgcacttggttgtacgatgtgttttccctagcttca
SEQ ID NO: 8    1  atgctctctcattagctctcttcctcttcctcttcctcttggttgtacgatgtgttttccctagcttca
SEQ ID NO: 5    1  atgctctctcattagctctcttcctcttcctcttcctcttggttgtacgatgtgttttccctagcttca
                   *********************************************** ***************

SEQ ID NO: 2   71  gtggggtagacgttcgtgttactttcctcagccacttgttgaaggagtttgacaaaaagttgatcactgc
SEQ ID NO: 8   71  gtggggtagacgttcgtgttactttcctcagccacttgttgaaggagtttgacaaaaagttgatcactgc
SEQ ID NO: 5   71  gtggggtagacgtccgtgttactttcctcagccacttgttgaaggagtttgacaaaaagttgatcactgc
                   ************* **************************************************

SEQ ID NO: 2  141  tttcaaagacaacgagatcgagagaagtcgatcactggatcccgagcttaaacaagccattaaagattcg
SEQ ID NO: 8  141  tttcaaagacaacgagatcgagagaagtcgatcactggatcccgagcttaaacaagccattaaagattcg
SEQ ID NO: 5  141  tttcaaagacaacgagatcgagagaagtcgatcactggatcccgagcttaaacaagccattaaagattcg
                   *****************************************************************

SEQ ID NO: 2  211  aggatcgcagtggttatctctctcccaaaactatgcctcttcaagctgtgtctcttaatgagtgttagaga
SEQ ID NO: 8  211  aggatcgcagtggttatctctctcccaaaactatgcctcttcaagctgtgtctcttaatgagtgttagaga
SEQ ID NO: 5  211  aggatcgcggtggttatctctctcccaaaactatgcctcttcaagctgtgtctcttaatgagtgttagaga
                   ******** ********************************************************

SEQ ID NO: 2  281  tagtcaagtgtggtcaaatggtgatacctgttttctaccggttgatccttccacgtgaggaaacaaac
SEQ ID NO: 8  281  tagtcaagcgtggtcaaatggtgatacctgttttctaccggttgatccttccacgtgaggaaacaaac
SEQ ID NO: 5  281  tagtcaagcgtggtcaaatggtgatacctgttttctaccggttggatccttccacgtgaggaaacaaac
                   ******** ***********************************  ********************

SEQ ID NO: 2  351  cggtgacttgggtaagttctttgaagaaacatgcaacaacagagaagaagaagaaata---cagtgg
SEQ ID NO: 8  351  cggtgaattgggaaaatatttgaagaaacatgcaagaacatgcaagaacagaagaagaagtgataactcaatgg
SEQ ID NO: 5  351  cggtgacttcggaaatatttgaagaaacatgcaagaacatgcaagaacagaagaagaagtgataattcaatgg
                   ******  *  *  * ****************** *** *** *** ****************

SEQ ID NO: 2  418  aggagagctttgaccgatgtagccaatactctcgggtatcattcagtaaactggtacggttatgc---
SEQ ID NO: 8  421  aggagagctttgaccgatgtagccaatactctcgggtatcattcagtaaactggtacggttttatgcatc
SEQ ID NO: 5  421  aggagagctttgaccgatgtagccaatactctcgggtatcattcagtaaactggtacggttttatgcatc
                   ************************************************************  ****
```

Figure 1

```
SEQ ID NO: 2    485  ----ttctttttgaataaaggttagacttctgttgtttgctagggggtgatattatcttctttattgttaggg
SEQ ID NO: 8    491  atcattcttttgagtaaaggttagacttctgttgtttgctagggggtgatattatcttctttattgttaggg
SEQ ID NO: 5    491  atcattcttttgagtaaaggttagacttctgttgtttgctagggggtgatattatttcttaatgttaggg
                     *  ***************************************************************

SEQ ID NO: 2    550  gtaacgaagctgcaatgattgaagaaatcgccaatgatgtttttgataaactacttttaacttcatcgaa
SEQ ID NO: 8    561  gtaacgaagctgcaatgattgaagaaatcgccaatgatgtttttgataaactacttttaacttcatcgaa
SEQ ID NO: 5    561  gtaacgaagctgcaatgattgaagaaatcgccaatgatgtttttgataaactacttttaacttcatcgaa
                     ********************************************************************

SEQ ID NO: 2    620  ggattcagagaactttgtgtgggcatcgaagatcatgttgcaaaactgagtgagtgtattgctgcagtggacgcg
SEQ ID NO: 8    631  ggattcagagaactttgtgtgggcatcgaagatcatcttgcagaactgagtgagtgtattgctgcagtggacgcg
SEQ ID NO: 5    631  ggattcagagaactttgtgtgggcatcgaagatcatcttgcagaactgagtgagtgtactgttgcagtggacgcg
                     ****************************************  ***** * ** ************

SEQ ID NO: 2    690  gaggaagtgaggatggttggtttatggggttcctcaggatcggcaagactacaattgcaagagttctgt
SEQ ID NO: 8    701  gaggaagtgaggatggttggtttatggggttcctcaggatcggcaagactacaattgcaagagttctgt
SEQ ID NO: 5    701  gaggaagtgaggatggttggtttatggggttcctcaggatcggcaagactacaattgcaagagttctgt
                     ********************************************************************

SEQ ID NO: 2    760  ttcaacgactttctcgacacttccgaggtagcatttcatagacagggctttcgtatctaagactatgga
SEQ ID NO: 8    771  ttcaacgactttctcgacacttccgaggtagcatttcatagacagggctttcgtatctaagactatgga
SEQ ID NO: 5    771  ttcaacgactttctcgacacttccgaggtagcatttcatagacagggctttcgtatctaagactatgga
                     ********************************************************************

SEQ ID NO: 2    830  aattttcaaggcagctaatccggacgactataacatgaagctgcatttgcaaagaaattttcctatctgaa
SEQ ID NO: 8    841  aattttcaaggcagctaatccggacgactataacatgaagctgcatttgcaaagaaattttcctatctgaa
SEQ ID NO: 5    841  aattttcaaggcagctaatccggacgactataacatgaagctgcatttgcaaagaaattttcctatctgaa
                     ********************************************************************

SEQ ID NO: 2    900  atcttaggtaaaggagacataaagataaatcatttgagtgcagttggggagaggctgaagatcagaaag
SEQ ID NO: 8    911  atcttaggtaaaggagacataaagataaatcatttgagtgcagttggggagaggctgaagatcagaaag
SEQ ID NO: 5    911  atcttaggtaaaggagacataaagataaatcatttgagtgcagttggggagaggctgaagatcagaaag
                     ********************************************************************
```

Figure 1 - continued

| | | |
|---|---|---|
| SEQ ID NO: 2 | 970 | ttcttattttcattgatgatttgatgatcaagttgtgctagaagcccttggttggtcaaactcaatggtt |
| SEQ ID NO: 8 | 981 | ttcttattttcattgatgatttgatgatcaagttgtgctagaagcccttggttggtcaaactcaatggtt |
| SEQ ID NO: 5 | 981 | ttcttattttcattgatgatttgatgatcaagttgtgctagaagcccttggttggtcaaactcaatggtt |
| | | ********************************************************************** |
| SEQ ID NO: 2 | 1040 | tggaagtgggagcagaatcgttgtggttacaaatgataagcagtatctaagggcccatgggattaatcac |
| SEQ ID NO: 8 | 1051 | tggaagtgggagcagaatcgttgtggttacaaatgataagcagtatctaagggcccatgggattaatcac |
| SEQ ID NO: 5 | 1051 | tggaagtgggagcagaatcgttgtggttacaaatgataagcagtatctaagggcccatgggattaatcac |
| | | ********************************************************************** |
| SEQ ID NO: 2 | 1110 | atttacaaggtctgtctcccaactaaaaagctagctgttgagatgttatgtcgatctgctttcaggaaaa |
| SEQ ID NO: 8 | 1121 | atttacgaggtctgtctcccaactgaaaaccagctgttgagatgttatgtcgatctgctttcaggaaaa |
| SEQ ID NO: 5 | 1121 | atttacgaggtctgtctcccaactgaaaaccagctgttgagatgttatgtcgatctgctttcaggaaaa |
| | | ******* ***************** **** ************************************** |
| SEQ ID NO: 2 | 1180 | aggctgcacctgaaggttttgaggagcttgtagctaaagttacaggactgctgtagtcttccttagg |
| SEQ ID NO: 8 | 1191 | aggctgcacctgaaggttttgaggagcttgtagctaaagttacaggactgctgtagtcttccttagg |
| SEQ ID NO: 5 | 1191 | aggctgcacctgaaggttttgaggagcttgtagctaaagttacaggactgctgtagtcttccttagg |
| | | ********************************************************************** |
| SEQ ID NO: 2 | 1250 | tcttaatgttttgggttcatatctacggggaaggagaagtactgatgatttgttgccaaggctt |
| SEQ ID NO: 8 | 1261 | tcttaatgttttgggttcatatctacggggaaggagaagtactgatgatttgttgccaaggctt |
| SEQ ID NO: 5 | 1261 | tcttaatgttttgggttcatctctacggggaaggagaagtactgatgatttgttgccaaggctt |
| | | ******************* ************************************************* |
| SEQ ID NO: 2 | 1320 | cagaatggtttagatgggaaaattgagaagacattgagagtcagctacgatgattaacaagcgaagaag |
| SEQ ID NO: 8 | 1331 | cagaatggtttagatgggaaaattgagaagacattgagggtcagctacgatgattaacaagcgaagaag |
| SEQ ID NO: 5 | 1331 | cggaattgtttagatgggaaaattgagaagacattgagagtcagctacgatgattaacaagcgaagaag |
| | | * *** ******************************** ***************************** |
| SEQ ID NO: 2 | 1390 | ataaagcgttattcgccatattgcatgcctttccagtgggaaaaagtcacatacctgaagttgctgct |
| SEQ ID NO: 8 | 1401 | ataaagcttatttcgccatatcgcatgcctttccaatggaaaaaagtcacatacctgaagttgctgct |
| SEQ ID NO: 5 | 1401 | ataaagccttatttcgccatatcgcatgcctttcaatggtgcaacagtcacatacctgaagtgtgct |
| | | ******* ***** ******* ************ *** *** **************** **** |

Figure 1 - continued

```
SEQ ID NO: 2    1460   cgctgatagtgtggggttgagtgttacggttgggctgtggaaaacctagctgataagtccctcattcatgtaaga
SEQ ID NO: 8    1471   cgctgatagtgtggggttgagtgttacggttgggctgtggaaaacctagctgataagtccatcattcatgtaagt
SEQ ID NO: 5    1471   cactgatagtgtggggttgagtgttaatgtggggctgtggaaaacctagctgataagtccctcattcatgaaaga
                       ************************ **** ***********************************   **

SEQ ID NO: 2    1530   gaggattatgtgaagatgcaccgtttgttagaagagatgggtagacgtattgttaggcttgacgagcctg
SEQ ID NO: 8    1541   acgaattatgtgtgatgcaccgtttgttagaagagagatgggtagaggtattgttaggcttgacgagcctg
SEQ ID NO: 5    1541   gaggattatgtggagatgcaccgtttgttagaagagatgggtagacgtattgttaggcttgaggagcctg
                         ********  ******************** *** ******* *****************  ******

SEQ ID NO: 2    1600   aaaaacgagaatttctggtggacgcacaagatatctgtgtgactcagtcaagacactgtaagttatct
SEQ ID NO: 8    1611   aaaaacgagaatttctggtggacgcacaagatatctgtgtgactcagtcaagacactgtaagttatct
SEQ ID NO: 5    1611   aaaaacgagaatttctggtggacgcacaagatatctgtgtgactcagtcaagacactgtaagttatct
                       *****************************************************************

SEQ ID NO: 2    1670   cttatgttcgtgctcctttcagtcaataaataagcatgccatttatagagcaaaactaatac
SEQ ID NO: 8    1681   cttatgttcgtgctcctttcagtcaataaataagcatgccatttatagagcaaaactaatac
SEQ ID NO: 5    1681   cttatgttcgtgctcctttcacagtcaataaataagcatgccatttatagagcaaaactaatac SEQ ID NO: 2    1740   ttgatatattataattttcaggtactcataagatattgggtataaaattgaatattgatgagattgatg
SEQ ID NO: 8    1751   ttgatatattataattttcaggtactcataagatattgggtataaaattgaatattgatgagattgatg
SEQ ID NO: 5    1751   ttgatatattataattttcaggtactcataagatattgggtataaaattgaatattgatgagattgatg
                       **********************************************************************

SEQ ID NO: 2    1810   aactgaatgtgcatgagaatgccttcaaaggatgcgcaatctgcgtttcctggaaattcactcacaaaa
SEQ ID NO: 8    1821   aactgaatgtgcatgagaatgccttcaaaggatgcgcaatctgcgtttcctggaaattcactcacaaaa
SEQ ID NO: 5    1821   aactgaatgtgcatgagaatgccttcaaaggatgcgcaatctgcgtttcctggaaattcactcacaaaaa
                       *********************************************************************

SEQ ID NO: 2    1880   ccgtcatgagtttggaaacgaagaagtttagaattcacttacctgaaaacttcgactatttgcctcctaaa
SEQ ID NO: 8    1891   ccgtcatgagtttggaaacgaagaagttagaattcacttacctgaaaacttcgactatttgcctccaaaa
SEQ ID NO: 5    1891   gcgttatgtgtttggaaagaagaagttagaataccaattcacttacctgaaaacttcgactatttgcctccaaaa
                          *  *** ********  *******  ***  *  ****************************** ***
```

Figure 1 - continued

```
SEQ ID NO: 2    1950   cttaaaatattggattggtatgaatatccaatgagatgtctgccttctaagtttcgtcctgaaaactcg
SEQ ID NO: 8    1961   cttaaaatattggattggtttggtatgaatatccaatgagatgtctgccttctaagtttcgtcctgaaaaactcg
SEQ ID NO: 5    1961   cttaaaatattggattggtatgaatatccaatgagatgtctgccttctaagtttcgtcctgaaaaactcg
                       * ********************************************************* ********

SEQ ID NO: 2    2020   tcaagctcaaaatggtgaatagcaagctcgagaagctcgtgggaaggattgtgtaagttttgagaatag
SEQ ID NO: 8    2031   tcaagctcaaaatggtgaatagcaagctcgagaagctcgtgggaaggattgtgtaagttttgagaatag
SEQ ID NO: 5    2031   tcaagctcaaaatggtgaatagcaagctcgagaagctcgtggaaaggattgtgtaagttttgagaatag
                       ***********************************************************************

SEQ ID NO: 2    2090   tttgtgatgttatttgtagtaagactaatcttattttttggatgacaatcttgttctactgagc
SEQ ID NO: 8    2101   tttgtgatgttatttgtagtaagactaatcttattttttggatgacaatcttgttctactgagc
SEQ ID NO: 5    2101   tttgtgatgttattagtagtaagactaatcttgattttttggatgacaatcttgttctactgagc
                       ****************** ************* ********************************

SEQ ID NO: 2    2160   tcatgtgttctgtccttttttt---ttgttgagtacagtcgcttacatgtcttaaaagatgaatat
SEQ ID NO: 8    2171   tcatgtgttctgtccttttttt---ttgttgagtacagtcgcttacatgtcttaaagagatgatat
SEQ ID NO: 5    2171   tcatgtgttgtcctttttttattgtttgttgagtacagtcgcttacatgtcttaataagatgatat
                       ********* ************   *************************** * ***** ***

SEQ ID NO: 2    2227   gtcgggatctcaaaacttgatagaaatgccagatcttcaaaggccaccaatctggagacactatcTT
SEQ ID NO: 8    2238   gtcgggatctcacaaacttgatagaaatgccagatcttcaaaggccaccaatctggagacacttaatgtt
SEQ ID NO: 5    2241   gtcggcatctcaaaacttgatagaaatgccagatcttcaaaggccaccaatctggagacacttaaactt
                       ***** ****** ***************************************** ***  *

SEQ ID NO: 2    2297   gaggatttgctttagtttggtcaagcttcctctattccacaccccaacaaactgacgacattaatct
SEQ ID NO: 8    2308   ggggcttgctatagtttggt---------------------------------------------
SEQ ID NO: 5    2311   cggaattgctatagttggtcaagcttcctctattccacatccaacaaactgacgacattaaact
                            ***** *  *** **

SEQ ID NO: 2    2367   tgaagaactgtcgaaatgtggagactattccaattgcattagcctcaaatctcttaaaaacctacgtac
SEQ ID NO: 8    2308   ----------------------------------------------------
SEQ ID NO: 5    2381   tgaagaactgtcgaaatctggagactattccaattgcattagcctcaaatctcctcaaaaacctaaatac
                       ****************  ************************************ **  ********
```

Figure 1 - continued

| | | |
|---|---|---|
| SEQ ID NO: 2 | 2437 | tgatggttgctcacggatgaggactttcccccaaatctcaagcaccatcgaagatgtctacatagccgca |
| SEQ ID NO: 8 | 2328 | ------------------------gacttttcccccaaatctcaagcaccatcgtagatgtcgacatagccgga |
| SEQ ID NO: 5 | 2451 | taaaggatgctcacggatgaggactttcccccaaatctcaaccagcatcgtagatgtcgacatagccgca |
| | | *  *   ************************ ** ** ********* ***** |

| | | |
|---|---|---|
| SEQ ID NO: 2 | 2507 | acatccattgaagaaatacctcaaatttgagtttgtgtttcgagaatctccatacctttacgatgcaca |
| SEQ ID NO: 8 | 2377 | acatccattgaagaaatacctcaaatttgagtttgtgtttcgagaatctccatacctttaagatgcaca |
| SEQ ID NO: 5 | 2521 | acatccattgaagaaatacctcaaatttgagtttgtgtttcgagagtctccatacctttacgatgcaca |
| | | ********************************************* ************ ****** |

| | | |
|---|---|---|
| SEQ ID NO: 2 | 2577 | gcccaaagaaaactatgggaaagagtgcaggtatgtgtagttccaaactttgtgtgtttctccaatctg |
| SEQ ID NO: 8 | 2447 | gcccaaagaaaactatcggaaagagtgcaggtatgtgtagttccaaactttgtgtgtttctccaatctg |
| SEQ ID NO: 5 | 2591 | gcccaaagaaaactatgggaaagagtgcaggtatgtgtagttccaaactttgtgtgtttctccaatctg |
| | | **************** ************************************************** |

| | | |
|---|---|---|
| SEQ ID NO: 2 | 2647 | ttttacgttatagatattagatgattttgtgtatttggttataatttatcggagggaaga |
| SEQ ID NO: 8 | 2517 | ttttacgttatagatattagatgattttgtgtatttggtgaaactaaggttataatttatcggagggaaga |
| SEQ ID NO: 5 | 2661 | ttttacgttatagatattagatgattttgtgtatttggtgcaatgaaactaaggttataatttatcggagggaaga |
| | | **************************************          ** ********************** |

| | | |
|---|---|---|
| SEQ ID NO: 2 | 2717 | agagtagcgctgaatatgattttgtgtatttggttcagcttcttactctcctcacgacgatcatgtctcc |
| SEQ ID NO: 8 | 2587 | agagtagcgctgaatatgattttgtgtatttggttcagcttcttactctcctcacgccgatcatgtctcc |
| SEQ ID NO: 5 | 2731 | agagtagcgctgaatatgattttgtgtatttggttcagcttcttactctcctcacgacgatcatgtctcc |
| | | ******************************************************** ************ |

| | | |
|---|---|---|
| SEQ ID NO: 2 | 2787 | ctctttgtggtatctcggataacctggcttggtggagcttccttcttcatttaagaatctc |
| SEQ ID NO: 8 | 2657 | ctctttgtggtatctcggataacctggcttggtggagcttccttcttcatttaagaatctc |
| SEQ ID NO: 5 | 2801 | ctctttgtggtatctcggatcaccaggcttgtgtgagcttccttcttcatttaagaatctc |
| | | ******************** *** ****** * ************************** |

| | | |
|---|---|---|
| SEQ ID NO: 2 | 2857 | cataacctgaggagattgaaattagaaactgcgtaaatctgaaactcttcccaccggaatcaacctcg |
| SEQ ID NO: 8 | 2727 | cataaactgagagagattgaaaattagaaactgcgtaaatctgaaactcttcccaccggaatcaacctcg |
| SEQ ID NO: 5 | 2871 | cataacttgcagatattgaaaattagtaactgcgtaaatctgaaactcttcccaccggaatcaacctcg |
| | | ****** **        ********* *********************************************** |

Figure 1 - continued

```
SEQ ID NO: 2   2927  gatctctcaaaaatcctagatctcaggggatgctcacggttgaggactttcctgatatctcaaccacat
SEQ ID NO: 8   2797  gatctctcgagagtagatctaagggatgctcacggttgagaactttcctgatatctcaaccaacat
SEQ ID NO: 5   2941  gatctctctggcaactagatctcagtgatgctcacggttgagaactttcctgatatctcaaccaacat
                     *******   *                       ****************************** ****

SEQ ID NO: 2   2997  cacacatctttatctaagcggaacagggattgaagagattccttgttctcgattgagaaattctccaggctt
SEQ ID NO: 8   2867  caaaaacctcgatctcagcgaacagcagcagcagcagcagcagaagagattccttgttgattgagaaattctccaggctt
SEQ ID NO: 5   3011  catagttctcgatctcagcgaacagcagcagcagcagccatcgaagagattccttgttggattgagaaattctctaacctt
                     **  ****                          ****  ***   *****   **********************

SEQ ID NO: 2   3067  ggctccctacatatgaacgatgcaaacaatttggaatatgtaaacctaaaccttttaaactcaaacatc
SEQ ID NO: 8   2937  tactccctacggatgaagggatgcaacacagtcagcgcaacaatttggaatatgtaaacatttctaaaactcaaatatc
SEQ ID NO: 5   3081  aactcccttaggatgaagggatgcaacagcagcagcagcaacaatttggaatatgtaaacattctaaaactcaaacatc
                         ****   ***** ** **  * **   ******************  * ***********  ***

SEQ ID NO: 2   3137  ttcacgaagtcgacttttcagactgcaagt-----------------------------------
SEQ ID NO: 8   3007  ttttcgaagtcgacttttcagactgcaagtcattgactgactgcagctagctagcgaataatcgtccaagagaaag
SEQ ID NO: 5   3151  ttcagaaagtagacttttcagactgcaagtcattgactgactgcagctagcgaataatcgtccaagagaaag
                     **   *** ** **************** *****

SEQ ID NO: 2   3167  ----------------------------gcttaaacttggatcaagaa
SEQ ID NO: 8   3077  tgccttgagttattaccacagtttcgacattggtatcgatttcaccaagtgctaaacttgctaaacttggatcaagaa
SEQ ID NO: 5   3221  tgccttgagttattaccacatgctacattggtatcgatttcaccaagtgctaaacttgctaaacttggatcaagaa
                                                              ****************************

SEQ ID NO: 2   3187  gctctgtttcaaaagaaaacatattcagtttgtcaactgaagttgtcaggtgaagaagtgccttcatatt
SEQ ID NO: 8   3147  gctctgtttcaaaagaaaacatattcggttgtgtcaactgaagttgtcaggtgaagaagtgccttcatatt
SEQ ID NO: 5   3291  gctctgtttcaaaagaaaacatatttttggttgtcatctgaagttgtcaggtgaagaagtgccttcatatt
                     ************************   *   *    ***********************************

SEQ ID NO: 2   3257  tcacgcaccgtactactggaacctcctctctccaccattcctcacttcacagctgtatctcacaatc
SEQ ID NO: 8   3217  tcacgcaccgtactactggaacctcctctctccaccattccttcacttcacagctgtctctcacaacc
SEQ ID NO: 5   3361  tcactcaccgtactactggaacctcctctctcctccaccattccttcacttcacagctgtctctcacaacc
                     ***  ****************************   *********  *****************  ****
```

Figure 1 - continued

```
SEQ ID NO: 2    3327  attcctccgattcagggcttgtattgtgtttgattcggacaaggacaatgagtcatatagcagatgtgcc
SEQ ID NO: 8    3287  attcctccgattcagggcttgcattgtgtttgtttgattc------gcacaatgagacatatagcaaatgtgtc
SEQ ID NO: 5    3431  attcctcctattcagggcttgtattgtgtttgtttgattcggacaag-----gagacatatagcgatgtgtc
                      *********** ********** ************ ****          ********** **** ****

SEQ ID NO: 2    3397  tttagattcaaaggcagtttttcggaactgctctgattcctataatcaggcacaagacttctgcgcagtca
SEQ ID NO: 8    3351  tttagattcaaaggcagtttttcagaactgctctgattcctataatcaggcacaagacttctgcgcagtca
SEQ ID NO: 5    3495  tttagattcaaaggcagtttttcggaactgctctgattcctataatcaggcacaagacttctgcgcagtca
                      ********************** ******************************************

SEQ ID NO: 2    3467  cggatgattataagatccgttcatataagaagatggttgtctgcttgtattagactaccagatgtctca
SEQ ID NO: 8    3421  cggaggattatttgatctattcatatgagaagatggttgtctgtttgtattagactaccagatgtctca
SEQ ID NO: 5    3565  cggatgattatgagatcaattcatcatgagaagatggttgtctgtttgtattagactaccagatgtctca
                      ****   ****  *** * **** ** *************** *********************

SEQ ID NO: 2    3537  aatcccttagaaatgaacttcgatctgcctgatctgaagattcatattgattattgtcgttctg---ct
SEQ ID NO: 8    3491  aatcccttagaaatgaacttcgatctgcctgatctgaagattcatattgttgttgattgtttatataatg---ct
SEQ ID NO: 5    3635  aatcccttagaaatgaactgaatcgatctgcctgaagattcatattgttgattgttttaatgatgct
                      ****************         * *  **  *    *  *  ** *      *     **

SEQ ID NO: 2    3604  aaaataaaaggatggggtatacgaatcttagagaggagactgttcatcggcagacaaccgacttggttatc
SEQ ID NO: 8    3558  aaaataaaaggatggggtatacgaatcttagagaggagactgttcatcggcagacaaccgacttggttatc
SEQ ID NO: 5    3705  aaaataaaaggatggggtatacgaatcttagagaggagactgttcatcggcagacaaccgacttggttatc
                      *****************************************************************

SEQ ID NO: 2    3674  caaacattctaccacatgttttttgaagccgatgaatgcaat--gaggctggtggtgaatgtgggaggcaaatg
SEQ ID NO: 8    3628  caaacattctaccacatgttttttgaagccgatgaatgcaatatgaggctggtggtgaatgtg-gaggcaaatg
SEQ ID NO: 5    3775  caaacattctaccacatgttttttgaagccgatgaatgcaatatgaggctggtggtgaatgtg-gaggcaaatg
                      ***********************************************   ************ ******

SEQ ID NO: 2    3742  atgtagtgacggaaagaagcgggtaaagg-cattaatcatgaacttatcacagtatttctatatcataa
SEQ ID NO: 8    3697  atgcagtgacggaaagaagcgggtaaagg--cattaatcatgaacttatcacagtatttctatatcataa
SEQ ID NO: 5    3844  atgcagtgacggaaagaagcgcggtaaagg cattaatcatgaacttatcacagtatttctatatcataa
                      *** ****************  *******  ********************************
```

```
SEQ ID NO: 2    3811  tttcttgtactgagagcatctaaaa-cttttttt-cttttctgcagatttcgtgaataaactttgattgtgttaggtt
SEQ ID NO: 8    3766  tttcttgtactgagagcatctaaaa-cttttttt-cttttctgcagatttcgtgaataagtttgattgtgttaggtt
SEQ ID NO: 5    3914  tttcttgtactgagagcatctaaaattcttttttctttttctgcagatttcgtgaataaagtttgattgtgttaggtt
                      ***************************  *******   ******************************* ***************

SEQ ID NO: 2    3880  gtaacgcagagcatctaaaattaggaattaagagagattcccatccaacttgcttgtgatcttagtatg
SEQ ID NO: 8    3835  gtaacgcagagcatctaaaattaggaattaagagagagttcccatccaacttgcttgtgatcttagtatg
SEQ ID NO: 5    3984  gtaacgcagagcatctaaaattaggaattaagagagagttcccatccaacttgcttgtgatcttagtatg
                      *******************************************************************

SEQ ID NO: 2    3950  cggagaagtaagagcacaaatttgtgggaaggagtagtgcatgtatgttttcttcaaccttcctttcctttcctt
SEQ ID NO: 8    3905  cggagaagtaagagcacacaatatttgtgggaaggagtagtgcatgtatgtttttcttcaaccttcctttcctttcctt
SEQ ID NO: 5    4054  cggagaagtaagagcacacaatatttgtgggaaggagtagtgcatgtatgtttttcttcaaccttcctttcctttcctt
                      ******************  ***************************************************************

SEQ ID NO: 2    4020  -atactagttcttacaaaaatggttatgcctggcagatctctagaaatgacctaacattattgtgtac
SEQ ID NO: 8    3975  tatactagttcttacaaaaatggttatgcctggcagatctctagaaatgacctaacattattgtgtac
SEQ ID NO: 5    4124  -atactagttcttacaaaaatggttatgcctggcagatctctagaaatgacctaacttattgtgtac
                       **********************************************************  *************

SEQ ID NO: 2    4089  cttaaattctcaggcagtgcctctttctatcagagattgctcctgcacagctcaggggaggtctcaac
SEQ ID NO: 8    4045  cttaaattctcaggcagtgcctctttctatcagagattgttcctgcacagctcaaggggaggtctcaac
SEQ ID NO: 5    4193  cttaaattctcaggcagtgcctctttttctatcagagattgctcctgcacagctcaaggggaggtctcaac
                      *************************  ******************  **************** ****************

SEQ ID NO: 2    4159  attgtattccaactcatggtcacaattggaatcctaatagccaaccttgtcaactacttcactgccaccg
SEQ ID NO: 8    4115  attgtattccaactcatggtcacaattggaatcctaatagccaaccttgtcaactacttcactgccaccg
SEQ ID NO: 5    4263  attgtattccaactcatgtaacaattggaatcctaatagccaaccttgtcaactacttcactgccaccg
                      ****************** *********************************************

SEQ ID NO: 2    4229  ttcaccctaacgatggcgaatcgccctcggtggagccgcaatcccacggttatcctagtcttcggttc
SEQ ID NO: 8    4185  ttcaccctaacgatggcgaatcgccctcggtggagccgcaatcccacggttatcctcctcttgggttc
SEQ ID NO: 5    4333  ttcaccctaacgatggcgaatcgccctcggtggagccgcaatcccacggttatcctcctcttgggttc
                      ********************************************************   *** ** **
```

```
SEQ ID NO: 2    4299  actgatcatctgcgagactcccacgagcttcatagagcgcaa------------------
SEQ ID NO: 8    4255  actgatcatctgtgagaccgtgagacctcatagagcgcaacaacaaaaacgaagaaggcagagagaaactcta
SEQ ID NO: 5    4403  actgatcatctgtgagaccccgagacctcatagagcgcaacaacaaaaacgaagaaggcagagagaaactcta
                      **********************  ***** *****************

SEQ ID NO: 2    4xxx  -----------gtgtttga
SEQ ID NO: 8    4xxx  aggaagatcagagagagtttga
SEQ ID NO: 5    4xxx  aggaaaatcagagagagtttga
                                 *  *****
```

Figure 1 - continued

```
SEQ ID NO: 3    1  malslasspsscrtwlydvfpsfsgvdvrvtflshllkefdkkllitafkdneiersrsldpelkqaikds
SEQ ID NO: 6    1  malslasspsssrtwlydvfpsfsgvdvrvtflshllkefdkkllitafkdneiersrsldpelkqaikds
SEQ ID NO: 9    1  malslasspsssrtwlydvfpsfsgvdvrvtflshllkefdkkllitafkdneiersrsldpelkqaikds
                   ******* *******************************************************

SEQ ID NO: 3   71  riavvifsqnyassswclnelleivkcgmvipvtyrldpshvrkqtgdfgkifeetcnnkteeekii-qw
SEQ ID NO: 6   71  riavvifsqnyassswclnelleivkrgqmvipvfyrldpshvrkqtgdfgkifeetcknqkeeviiiqw
SEQ ID NO: 9   71  riavvifsqnyassswclnelleivkrgqmvipvfyrldpshvrkqtgefgkifeetcknqkeeviitqw
                   ************************** * ****** ************ ************** *  **

SEQ ID NO: 3  140  rraltdvantlgyhsvnwgneaamieeiandvldkllltsskdsenfvgiedhvaklsvllqldaeevrm
SEQ ID NO: 6  141  rraltdvantlgyhsvnwgneaamieeiandvldkllltsskdsenfvgiedhiaelsvllqldaeevrm
SEQ ID NO: 9  141  rraltdvantlgyhsvnwgneaamieeiandvldkllltsskdsenfvgiedhlaelsvllqldaeevrm
                   *****************************************************  * ************

SEQ ID NO: 3  210  vglwgssqigkttiarvlfqrlsrhfrgsifidrafvsktmeifkaanpddynmkihlqrnflseilqkg
SEQ ID NO: 6  211  vglwgssgigkttiarvlfqrlsrhfrgsifidrafvsktmeifkaanpddynmkihlqrnflseilgkg
SEQ ID NO: 9  211  vglwgssgigkttiarvlfqrlsrhfrgsifidrafvsktmeifkeanpddynmkihlqrnflseilgkg
                   ******* ************************************* ********************* **

SEQ ID NO: 3  280  dikinhlsavgerlknqkvlifiddfddqvvlealvggtqwfgssgsrivvvtndkqylrahginhiyvc
SEQ ID NO: 6  281  dikinhlsavgerlknqkvlifiddfddqvvlealvggtqwfgssgsrivvvtndkqylrahginhiyevc
SEQ ID NO: 9  281  dikinhlsaveerlknqkvlifiddfddqvvlealvggtqwfgssgsrivvvtndkqylrahginhiyevc
                   ********* *********************************************************  **

SEQ ID NO: 3  350  lptkklavemlcrsafrkkaapegfeelvakvtglagslpiglnvlgsylrgrdkeywmdllprlqngld
SEQ ID NO: 6  351  lptgnlavemlcryafrkkaapegfeelvakvtglagslpiglnvlgsslrgrdkeywmdllprlrncld
SEQ ID NO: 9  351  lptenlavemlcrsafrkkaapegfeelvakvtlngatvtglagslpiglnvlgrekkywmdllprlqngld
                   ***  ******** *****************                    * ********* *  **

SEQ ID NO: 3  420  gkiektlrvsydgltseedkalfrhiaclfqwekvtylklllladsglsvtvglenladkslihvredyvk
SEQ ID NO: 6  421  gkiektlrvsydgltseedkalfrhiaclfngatvtylklllkvltdsglsvnvglenladksliheredyve
SEQ ID NO: 9  421  gkiektlrvsydgltseedkalfrhiaclfqwkkvtylklllladsglsvtvglenladksliihvstnyvv
                   ******************************    ********  ****** ************   **
```

Figure 2

```
SEQ ID NO: 3   490  mhrlleemgrrivrldepekreflvdaagdicdvlsqdtgthkilgiklnideidelnvhenafkgmrnlir
SEQ ID NO: 6   491  mhrlleemgrrivrleepekreflvdaagdicdvlsqdtgthkilgiklnideidelnvhenafkgmrnlir
SEQ ID NO: 9   491  mhrlleemgrgivrldepekreflvdaagdicdvlsqdtgthkilgiklnideidelnvhenafkgmrnlir
                    ***********:**********************************************************

SEQ ID NO: 3   560  fleihsqnrhefgneevrihlpenfdylppklkildwyepmrclpskfrpeklvklkmvnsklekweg
SEQ ID NO: 6   561  fleihskkryvfgkeevpihlpenfdylppklkildwyepmrclpskfrpeklvklkmvnsklekwkg
SEQ ID NO: 9   561  fleihsqnrhefgneevrihlpenfdylpkklkildwfgypmrclpskfrpeklvklkmvnsklekweg
                    ******.::*.:**:*.***:*********.******:* *******************:*****:*

SEQ ID NO: 3   630  ivsltcikkmnmsgsqnliempdlskatnletlyledcfslvklpssiphpnklttlilkncrnvetipi
SEQ ID NO: 6   631  ivsltcinkmdmsasqnliempdiskatnletikirncyslvklpssiphpnklttinlikncrnietipi
SEQ ID NO: 9   631  ivsltcikemdmsgstnliempdlskatnletlnvgacyslv---------------------------
                    *******::**:**.:.**********:*******:  .****  ;

SEQ ID NO: 3   700  gislksiknlrtdgcsrmrtfpqisstiedvyigatsieeipsnlsicfenlhftmhspkklwervqli
SEQ ID NO: 6   701  gislksiknlntkgcsrmrifpqistsivdvdiaatsieeipsnlsicfeslhtftmhspkklwervqli
SEQ ID NO: 9   673  --------------tfpqisstivdvdiagtsieeipsnlsicfenlhtfkmhspkklserevqli
                                  ; ***** ::* ** .********************:.***.*******:****

SEQ ID NO: 3   770  tlilttimspsliwyldisdnpglveipssfknlhnlrrieirncvnletiptginlgsikildlrgcsrlr
SEQ ID NO: 6   771  tlilttimspsliwyldisdnpglveipssfknlhnlqiikisncvnletiptginlgsiwqidisgcsrlr
SEQ ID NO: 9   724  tltpimspslwylnlsdnpglveipssfknlhklerikirkirncvnletiptginlgsisrvdlrgcsrlr
                    **:* ******::****************** :: *:***:*********:.: :* **.*

SEQ ID NO: 3   840  tfpdisthithlylsgtqieeipcsiekfsrlgslhmngcnnleyvnlfklkihevdfsdck------
SEQ ID NO: 6   841  tfpdistniividlsetaieeipcwiekfsninslrmkgcnnleyvnlniskikhlqkvdfsdcksitga
SEQ ID NO: 9   794  tfpdistniknidlsetaieeipcwiekfsrlyslrmkgcnnleyvnlniskikylfevdfsdcksitga
                    *********  :*** *******.******:: **:*************::* ::* ******

SEQ ID NO: 3   905  --------------clnldqealfqktkclnldqealfqkktysvcqlkisgeevpsyfthrttgtsssltip
SEQ ID NO: 6   911  slnnrpresalsyyhicyigidftkclnldqealfqktkclnldqealfqkktyfgchlkisgeevpsyfthrttgtsssltip
SEQ ID NO: 9   864  swnnrpresalsyyhsfdigidftkclnldqealfqkktyfgcqlkisgeevpsyfthrttgtsssltip
                                  *******************:
```

Figure 2 – continued

```
SEQ ID NO: 3    950  llhsclsqsflrfraciivfdsdkdnesysrcafrrfkgsfrncsdsynqaqdfcavtddykirsykkdgcl
SEQ ID NO: 6    981  llhsclsqpfllfraciivfdsdk--etysdcvfrfkgsfrncsdsynqaqdfcavtddyeinsyekdgcl
SEQ ID NO: 9    934  llhsclsqpflrfraciivfds---hnetyskcvirfkgsfqncsdsynqaqdfcavtedyliysyekdgcl
                     *******;**:*********  . *.;:* ****** ****************:* **  ****

SEQ ID NO: 3   1020  lvldyqmsqiplemnfdgldlkihidyc--rsakikgwgirileedcssadnrlgypnilphvfeadecne
SEQ ID NO: 6   1049  fvldyqmsqiplemnfdrldlkihivdcfndakikgwgirileedcssadnrlgypnilphvfeadecn-
SEQ ID NO: 9   1002  fvldyqmsqiplemnfdgldlkihivdc--ynakikgwgirileedcssadnrlgypnilphvfeadecn-
                     ****************  ******* *    .:********************************

SEQ ID NO: 3   1089  adfvnkllivlgcnaehlklgikrdshptclwilvcgeavplflseiapaqlrgglnivfqlmvtigili
SEQ ID NO: 6   1118  ----mrlvnveandavtersgmrr-skstilwegvv-havplflseiapaqlrgglnivfqlmvtigili
SEQ ID NO: 9   1070  ----mrlvnveandavtersgmrr-skstilwegvv-havplflseivpaqlkgglnivfqlmvtigili
                         :*;  :  .:*      . *;;* *** :*      *********.***:***************

SEQ ID NO: 3   1159  anlvnyftatvhpngwrialggaaiptvilvfgsliicetptsfierkc----------
SEQ ID NO: 6   1182  anlvnyftatvhpngwrialggaaipavilllgsliicetptsliernkneegretlrkirg
SEQ ID NO: 9   1134  anlvnyftatvhpngsrialggaaipavilllgsliicetptsliernkneegretlrkirg
                     ***************.**********.****:************:**;  
```

Figure 2 - continued

SEQUENCE LISTING

<160> NUMBER OF SEQ ID NOS: 12

<210> SEQ ID NO 1
<211> LENGTH: 3623
<212> TYPE: DNA
<213> ORGANISM: Brassica napus

<400> SEQUENCE: 1

```
atggctctct cattagcttc ttctccttcc tcttgtcgca cttggttgta cgatgttttc      60
cctagcttca gtggggtaga cgttcgtgtt actttcctca gccacttgtt gaaggagttt     120
gacaaaaagt tgatcactgc tttcaaagac aacgagatcg agagaagtcg atcactggat     180
cccgagctta acaagccat  taaagattcg aggatcgcag tggttatctt ctcccaaaac     240
tatgcctctt caagctggtg tcttaatgag ttgttagaga tagtcaagtg tggtcaaatg     300
gtgatacctg ttttctaccg gttggatcct tcccatgtga ggaaacaaac cggtgacttt     360
ggtaagttct tgaagaaac  atgcaacaac aaaacagagg aagagaaaat acagtggagg     420
agagctttga ccgatgtagc caatactctc gggtatcatt cagtaaactg gggtaacgaa     480
gctgcaatga ttgaagaaat cgccaatgat gttttggata actactttt  aacttcatcg     540 aaggattcag agaactttgt gggcatcgaa gatcatgttg caaaactgag tgtattgctg     600
cagttggacg cggaggaagt gaggatggtt ggtttatggg gttcctcagg atcggcaag      660 actacaattg caagagttct gtttcaacga cttctcgac  acttccgagg tagcattttc     720
atagacaggg ctttcgtatc taagactatg gaaattttca aggcagctaa tccgacgac      780 tataacatga agctgcattt gcaaagaaat ttcctatctg aaatcttagg taaaggagac     840
ataaagataa atcatttgag tgcagttggg gagaggctga agaatcagaa agttcttatt     900
ttcattgatg attttgatga tcaagttgtg ctagaagcct tggttggtca aactcaatgg     960
tttggaagtg ggagcagaat cgttgtggtt acaaatgata agcagtatct aagggcccat    1020
gggattaatc acatttacaa ggtctgtctc ccaactaaaa agctagctgt tgagatgtta    1080
tgtcgatctg ctttcaggaa aaaggctgca cctgaaggtt ttgaggagct tgtagctaaa    1140
gttacaggac ttgctggtag tcttcctta  ggtcttaatg ttttgggttc atatctacgg    1200
ggaagggaca aggagtactg gatggatttg ttgccaaggc ttcagaatgg tttagatggg    1260
aaaattgaga agacattgag agtcagctac gatggattaa caagcgaaga agataaagcg    1320
ttatttcgcc atattgcatg cctttttccag tgggaaaaag tcacatacct gaagttgctg    1380
ctcgctgata gtgggttgag tgttacggtt gggctggaaa acctagctga taagtccctc    1440
attcatgtaa gagaggatta tgtgaagatg caccgtttgt tagaagagat gggtagacgt    1500
attgttaggc ttgacgagcc tgaaaaacga gaatttctgg tggacgcaca agatatctgt    1560
gatgtactca gtcaagacac tggtactcat aagatattgg gtataaaatt gaatattgat    1620
gagattgatg aactgaatgt gcatgagaat gccttcaaag ggatgcgcaa tctgcgtttc    1680
ctggaaattc actcacaaaa ccgtcatgag tttggaaacg aagaagttag aattcactta    1740
cctgaaaact tcgactattt gcctcctaaa cttaaaatat tggattggta tgaatatcca    1800
atgagatgtc tgccttctaa gtttcgtcct gaaaaactcg tcaagctcaa aatggtgaat    1860
agcaagctcg agaagctgtg ggaagggatt gtgtcgctta catgtcttaa aaagatgaat    1920
atgtcgggat ctcaaaactt gatagaaatg ccagatcttt caaaggccac caatctggag    1980
acactatatc ttgaggattg ctttagtttg gtcaagcttc cttcctctat tccacacccc    2040 aacaaaactga cgacattaat cttgaagaac tgtcgaaatg tggagactat tccaattggc    2100
```

| | |
|---|---:|
| attagcctca aatctcttaa aaacctacgt actgatggtt gctcacggat gaggactttt | 2160 |
| ccccaaatct caagcaccat cgaagatgtc tacataggcg caacatccat tgaagaaata | 2220 |
| ccttcaaatt tgagtttgtg tttcgagaat ctccatacct ttacgatgca cagcccaaag | 2280 |
| aaactatggg aaagagtgca gcttcttact ctcctcacga cgatcatgtc tccctctttg | 2340 |
| tggtatctgg atctctcgga taaccctggc ttggtggagc ttccttcttc atttaagaat | 2400 |
| ctccataacc tgaggagatt ggaaattaga aactgcgtaa atctggaaac tcttcccacc | 2460 |
| ggaatcaacc tcggatctct caaaatccta gatctcaggg gatgctcacg gttgaggact | 2520 |
| tttcctgata tctcaaccca catcacacat ctttatctaa gcggaacagg gattgaagag | 2580 |
| attccttgtt cgattgagaa attctccagg cttggctccc tacatatgaa cggatgcaac | 2640 |
| aatttggaat atgtaaacct aaaccttttt aaactcaaac atcttcacga agtcgacttt | 2700 |
| tcagactgca agtgcttaaa cttggatcaa gaagctctgt ttcaaaagaa aacatattca | 2760 |
| gtttgtcaac tgaagttgtc aggtgaagaa gtgccttcat atttcacgca ccgtactact | 2820 |
| ggaacctcct cctctctcac cattcctcta cttcacagct gtatctcaca atcattcctc | 2880 |
| cgattcaggg cttgtattgt gtttgattcg gacaaggaca atgagtcata tagcagatgt | 2940 |
| gcctttagat tcaaaggcag ttttcggaac tgctctgatt cctataatca ggcacaagac | 3000 |
| ttctgcgcag tcacggatga ttataagatc cgttcatata agaaggatgg ttgtctgctt | 3060 |
| gtattagact accagatgtc tcaaatccct ttagaaatga acttcgatgg cctggatctg | 3120 |
| aagattcata ttgattattg tcgttctgct aaaataaaag gatggggtat acgaatctta | 3180 |
| gaggaggact gttcatcggc agacaaccga cttggttatc caaacattct accacatgtt | 3240 |
| tttgaagccg atgaatgcaa tgaggctgat tcgtgaata aacttttgat tgtgttaggt | 3300 |
| tgtaacgcag agcatctaaa attaggaatt aagagagatt cccatccaac ttgcttgtgg | 3360 |
| atcttagtat gcggagaagc agtgcctctt tttctatcag agattgctcc tgcacagctc | 3420 |
| aggggaggtc tcaacattgt attccaactc atggtcacaa ttggaatcct aatagccaac | 3480 |
| cttgtcaact acttcactgc caccgttcac cctaacggat ggcgaatcgc cctcggtgga | 3540 |
| gccgcaatcc ccaccgttat cctagtcttc ggttcactga tcatctgcga gactcccacg | 3600 |
| agcttcatag agcgcaagtg ttg | 3623 |

<210> SEQ ID NO 2
<211> LENGTH: 4749
<212> TYPE: DNA
<213> ORGANISM: Brassica napus

<400> SEQUENCE: 2

| | |
|---|---:|
| gccagctatt taggtgacac tatagaatac tcaagctatg catcaagctt ggtaccgagc | 60 |
| tcggatccac tagtaacggc cgccagtgtg ctggaattcg ccctttgcg ctacactcca | 120 |
| atctgacaat ttatatggac taacattctt cagaagatca atcaccaagt ccttcttttc | 180 |
| cttcatatta tttttgctcc tatctctatg gctctctcat tagcttcttc tccttcctct | 240 |
| tgtcgcactt ggttgtacga tgttttcct agcttcagtg gggtagacgt tcgtgttact | 300 |
| ttcctcagcc acttgttgaa ggagtttgac aaaaagttga tcactgcttt caagacaac | 360 |
| gagatcgaga gaagtcgatc actggatccc gagcttaaac aagccattaa agattcgagg | 420 |
| atcgcagtgg ttatcttctc ccaaaactat gcctcttcaa gctggtgtct taatgagttg | 480 |
| ttagagatag tcaagtgtgg tcaaatggtg atacctgttt tctaccggtt ggatccttcc | 540 |

```
catgtgagga aacaaaccgg tgactttggt aagttctttg aagaaacatg caacaacaaa    600
acagaggaag agaaaataca gtggaggaga gctttgaccg atgtagccaa tactctcggg    660
tatcattcag taaactggta cggttttatg cttcttttga ataaaggtta gacttctggt    720
tgctaggggg tgatattatc tttcttattg ttaggggtaa cgaagctgca atgattgaag    780
aaatcgccaa tgatgttttg gataaactac ttttaacttc atcgaaggat tcagagaact    840
ttgtgggcat cgaagatcat gttgcaaaac tgagtgtatt gctgcagttg gacgcggagg    900
aagtgaggat ggttggttta tggggttcct cagggatcgg caagactaca attgcaagag    960
ttctgtttca acgactttct cgacacttcc gaggtagcat tttcatagac agggctttcg   1020
tatctaagac tatggaaatt ttcaaggcag ctaatccgga cgactataac atgaagctgc   1080
atttgcaaag aaatttccta tctgaaatct taggtaaagg agacataaag ataaatcatt   1140
tgagtgcagt tggggagagg ctgaagaatc agaaagttct tattttcatt gatgattttg   1200
atgatcaagt tgtgctagaa gccttggttg gtcaaactca atggtttgga agtgggagca   1260
gaatcgttgt ggttacaaat gataagcagt atctaagggc ccatgggatt aatcacattt   1320
acaaggtctg tctcccaact aaaaagctag ctgttgagat gttatgtcga tctgctttca   1380
ggaaaaaggc tgcacctgaa ggttttgagg agcttgtagc taaagttaca ggacttgctg   1440
gtagtcttcc tttaggtctt aatgttttgg gttcatatct acggggaagg gacaaggagt   1500
actggatgga tttgttgcca aggcttcaga atggtttaga tgggaaaatt gagaagacat   1560
tgagagtcag ctacgatgga ttaacaagcg aagaagataa agcgttattt cgccatattg   1620
catgcctttt ccagtgggaa aaagtcacat acctgaagtt gctgctcgct gatagtgggt   1680
tgagtgttac ggttgggctg gaaaacctag ctgataagtc cctcattcat gtaagagagg   1740
attatgtgaa gatgcaccgt tgttagaag agatgggtag acgtattgtt aggcttgacg   1800
agcctgaaaa acgagaattt ctggtggacg cacaagatat ctgtgatgta ctcagtcaag   1860
acactgtaag ttatctctta tgttcgtgct cctttcagtc aataaataag atttagagca   1920
tgccatttta taagcaaaac taatacttga tattatataa ttttcagggt actcataaga   1980
tattgggtat aaaattgaat attgatgaga ttgatgaact gaatgtgcat gagaatgcct   2040
tcaaagggat gcgcaatctg cgtttcctgg aaattcactc acaaaaccgt catgagtttg   2100
gaaacgaaga agttagaatt cacttacctg aaaacttcga ctatttgcct cctaaactta   2160
aaatattgga ttggtatgaa tatccaatga gatgtctgcc ttctaagttt cgtcctgaaa   2220
aactcgtcaa gctcaaaatg gtgaatagca agctcgagaa gctgtgggaa gggattgtgg   2280
taagttttga gaatagtttg tgatgttatt tgtagtaaga ctaatcttta ttttattttt   2340
tggatgacaa tcttgttcta ctgagctcat gtgttctgtt cctttttttt tttgttgagt   2400
acagtcgctt acatgtctta aaaagatgaa tatgtcggga tctcaaaact tgatagaaat   2460
gccagatctt tcaaaggcca ccaatctgga gacactatat cttgaggatt gctttagttt   2520
ggtcaagctt ccttcctcta ttccacaccc caacaaactg acgacattaa tcttgaagaa   2580
ctgtcgaaat gtggagacta ttccaattgg cattagcctc aaatctctta aaaacctacg   2640
tactgatggt tgctcacgga tgaggacttt tccccaaatc tcaagcacca tcgaagatgt   2700
ctacataggc gcaacatcca ttgaagaaat accttcaaat ttgagtttgt gtttcgagaa   2760
tctccatacc tttacgatgc acagcccaaa gaaactatgg aaagagtgca aggtatgtat   2820
gtagttccaa actttgtgtg tttctccaat ctgttttacg ttatagatat tagataatgg   2880
tgcaaatgaa actaaggtta tattgtattt atcggaggga agaagagtag cgctgaatat   2940
```

```
gattttgtgt atttggttca gcttcttact ctcctcacga cgatcatgtc tccctctttg    3000
tggtatctgg atctctcgga taaccctggc ttggtggagc ttccttcttc atttaagaat    3060
ctccataacc tgaggagatt ggaaattaga aactgcgtaa atctggaaac tcttcccacc    3120
ggaatcaacc tcggatctct caaaatccta gatctcaggg gatgctcacg gttgaggact    3180
tttcctgata tctcaaccca catcacacat ctttatctaa gcggaacagg gattgaagag    3240
attccttgtt cgattgagaa attctccagg cttggctccc tacatatgaa cggatgcaac    3300
aatttggaat atgtaaacct aaacctttt aaactcaaac atcttcacga agtcgacttt    3360
tcagactgca agtgcttaaa cttggatcaa gaagctctgt ttcaaaagaa acatattca    3420
gtttgtcaac tgaagttgtc aggtgaagaa gtgccttcat atttcacgca ccgtactact    3480
ggaacctcct cctctctcac cattcctcta cttcacagct gtatctcaca atcattcctc    3540
cgattcaggg cttgtattgt gtttgattcg acaaggaca atgagtcata tagcagatgt    3600
gcctttagat tcaaaggcag ttttcggaac tgctctgatt cctataatca ggcacaagac    3660
ttctgcgcag tcacggatga ttataagatc cgttcatata agaaggatgg ttgtctgctt    3720
gtattagact accagatgtc tcaaatccct ttagaaatga acttcgatgg cctggatctg    3780
aagattcata ttgattattg tcgttctgct aaaataaaag gatggggtat acgaatctta    3840
gaggaggact gttcatcggc agacaaccga cttggttatc caaacattct accacatgtt    3900
tttgaagccg atgaatgcaa tgaggctggt gaatgtggga ggcaaatgat gtagtgacgg    3960
aaagaagcgg gtaaaggcat taatcatgaa cttatcacag tattttctat atcataattt    4020
cttgtactga gacttttttt tcttttttctg cagatttcgt gaataaactt ttgattgtgt    4080
taggttgtaa cgcagagcat ctaaaattag gaattaagag agattcccat ccaacttgct    4140
tgtggatctt agtatgcgga gaagtaagag cacaaaattg tgggaaggag tagtgcatgt    4200
atgttttctt caaccttcct tcctttatac tagttcttac aaaaatggtt atgcctggca    4260
gatctctaga aatgacctaa cattattgtg tgtaccttaa attctcaggc agtgcctctt    4320
tttctatcag agattgctcc tgcacagctc aggggaggtc tcaacattgt attccaactc    4380
atggtcacaa ttggaatcct aatagccaac cttgtcaact acttcactgc caccgttcac    4440
cctaacggat ggcgaatcgc cctcggtgga gccgcaatcc ccaccgttat cctagtcttc    4500
ggttcactga tcatctgcga gactcccacg agcttcatag agcgcaagtg ttgaaaccag    4560
cgagtcgtcc acctttaatc attggaatgc ttctacagct tttccagcag tttagtggaa    4620
tcaatgctat tatgttctac gcaccggttt aagggcgaa ttctgcagat atccatcaca    4680
ctggcggccg ctcgagcatg catctagagg gcccaattcg ccctatagtg agtcgtatac    4740
aatcactgc                                                            4749
```

<210> SEQ ID NO 3
<211> LENGTH: 1207
<212> TYPE: PRT
<213> ORGANISM: Brassica napus

<400> SEQUENCE: 3

Met Ala Leu Ser Leu Ala Ser Ser Pro Ser Ser Cys Arg Thr Trp Leu
1               5                   10                  15

Tyr Asp Val Phe Pro Ser Phe Ser Gly Val Asp Val Arg Val Thr Phe
            20                  25                  30

Leu Ser His Leu Leu Lys Glu Phe Asp Lys Lys Leu Ile Thr Ala Phe
        35                  40                  45

```
Lys Asp Asn Glu Ile Glu Arg Ser Arg Ser Leu Asp Pro Glu Leu Lys
    50                  55                  60

Gln Ala Ile Lys Asp Ser Arg Ile Ala Val Val Ile Phe Ser Gln Asn
65                  70                  75                  80

Tyr Ala Ser Ser Ser Trp Cys Leu Asn Glu Leu Leu Glu Ile Val Lys
                85                  90                  95

Cys Gly Gln Met Val Ile Pro Val Phe Tyr Arg Leu Asp Pro Ser His
                100                 105                 110

Val Arg Lys Gln Thr Gly Asp Phe Gly Lys Phe Phe Glu Glu Thr Cys
            115                 120                 125

Asn Asn Lys Thr Glu Glu Glu Lys Ile Gln Trp Arg Arg Ala Leu Thr
            130                 135                 140

Asp Val Ala Asn Thr Leu Gly Tyr His Ser Val Asn Trp Gly Asn Glu
145                 150                 155                 160

Ala Ala Met Ile Glu Glu Ile Ala Asn Asp Val Leu Asp Lys Leu Leu
                165                 170                 175

Leu Thr Ser Ser Lys Asp Ser Glu Asn Phe Val Gly Ile Glu Asp His
            180                 185                 190

Val Ala Lys Leu Ser Val Leu Leu Gln Leu Asp Ala Glu Glu Val Arg
            195                 200                 205

Met Val Gly Leu Trp Gly Ser Ser Gly Ile Gly Lys Thr Thr Ile Ala
210                 215                 220

Arg Val Leu Phe Gln Arg Leu Ser Arg His Phe Arg Gly Ser Ile Phe
225                 230                 235                 240

Ile Asp Arg Ala Phe Val Ser Lys Thr Met Glu Ile Phe Lys Ala Ala
                245                 250                 255

Asn Pro Asp Asp Tyr Asn Met Lys Leu His Leu Gln Arg Asn Phe Leu
        260                 265                 270

Ser Glu Ile Leu Gly Lys Gly Asp Ile Lys Ile Asn His Leu Ser Ala
            275                 280                 285

Val Gly Glu Arg Leu Lys Asn Gln Lys Val Leu Ile Phe Ile Asp Asp
        290                 295                 300

Phe Asp Asp Gln Val Val Leu Glu Ala Leu Val Gly Gln Thr Gln Trp
305                 310                 315                 320

Phe Gly Ser Gly Ser Arg Ile Val Val Thr Asn Asp Lys Gln Tyr
                325                 330                 335

Leu Arg Ala His Gly Ile Asn His Ile Tyr Lys Val Cys Leu Pro Thr
            340                 345                 350

Lys Lys Leu Ala Val Glu Met Leu Cys Arg Ser Ala Phe Arg Lys Lys
        355                 360                 365

Ala Ala Pro Glu Gly Phe Glu Glu Leu Val Ala Lys Val Thr Gly Leu
        370                 375                 380

Ala Gly Ser Leu Pro Leu Gly Leu Asn Val Leu Gly Ser Tyr Leu Arg
385                 390                 395                 400

Gly Arg Asp Lys Glu Tyr Trp Met Asp Leu Leu Pro Arg Leu Gln Asn
                405                 410                 415

Gly Leu Asp Gly Lys Ile Glu Lys Thr Leu Arg Val Ser Tyr Asp Gly
            420                 425                 430

Leu Thr Ser Glu Glu Asp Lys Ala Leu Phe Arg His Ile Ala Cys Leu
        435                 440                 445

Phe Gln Trp Glu Lys Val Thr Tyr Leu Lys Leu Leu Ala Asp Ser
450                 455                 460
```

```
Gly Leu Ser Val Thr Val Gly Leu Glu Asn Leu Ala Asp Lys Ser Leu
465                 470                 475                 480

Ile His Val Arg Glu Asp Tyr Val Lys Met His Arg Leu Leu Glu Glu
            485                 490                 495

Met Gly Arg Arg Ile Val Arg Leu Asp Glu Pro Glu Lys Arg Glu Phe
        500                 505                 510

Leu Val Asp Ala Gln Asp Ile Cys Asp Val Leu Ser Gln Asp Thr Gly
            515                 520                 525

Thr His Lys Ile Leu Gly Ile Lys Leu Asn Ile Asp Glu Ile Asp Glu
        530                 535                 540

Leu Asn Val His Glu Asn Ala Phe Lys Gly Met Arg Asn Leu Arg Phe
545                 550                 555                 560

Leu Glu Ile His Ser Gln Asn Arg His Glu Phe Gly Asn Glu Glu Val
            565                 570                 575

Arg Ile His Leu Pro Glu Asn Phe Asp Tyr Leu Pro Pro Lys Leu Lys
        580                 585                 590

Ile Leu Asp Trp Tyr Glu Tyr Pro Met Arg Cys Leu Pro Ser Lys Phe
        595                 600                 605

Arg Pro Glu Lys Leu Val Lys Leu Lys Met Val Asn Ser Lys Leu Glu
        610                 615                 620

Lys Leu Trp Glu Gly Ile Val Ser Leu Thr Cys Leu Lys Lys Met Asn
625                 630                 635                 640

Met Ser Gly Ser Gln Asn Leu Ile Glu Met Pro Asp Leu Ser Lys Ala
            645                 650                 655

Thr Asn Leu Glu Thr Leu Tyr Leu Glu Asp Cys Phe Ser Leu Val Lys
        660                 665                 670

Leu Pro Ser Ser Ile Pro His Pro Asn Lys Leu Thr Thr Leu Ile Leu
        675                 680                 685

Lys Asn Cys Arg Asn Val Glu Thr Ile Pro Ile Gly Ile Ser Leu Lys
        690                 695                 700

Ser Leu Lys Asn Leu Arg Thr Asp Gly Cys Ser Arg Met Arg Thr Phe
705                 710                 715                 720

Pro Gln Ile Ser Ser Thr Ile Glu Asp Val Tyr Ile Gly Ala Thr Ser
            725                 730                 735

Ile Glu Glu Ile Pro Ser Asn Leu Ser Leu Cys Phe Glu Asn Leu His
            740                 745                 750

Thr Phe Thr Met His Ser Pro Lys Lys Leu Trp Glu Arg Val Gln Leu
        755                 760                 765

Leu Thr Leu Leu Thr Thr Ile Met Ser Pro Ser Leu Trp Tyr Leu Asp
        770                 775                 780

Leu Ser Asp Asn Pro Gly Leu Val Glu Leu Pro Ser Ser Phe Lys Asn
785                 790                 795                 800

Leu His Asn Leu Arg Arg Leu Glu Ile Arg Asn Cys Val Asn Leu Glu
            805                 810                 815

Thr Leu Pro Thr Gly Ile Asn Leu Gly Ser Leu Lys Ile Leu Asp Leu
        820                 825                 830

Arg Gly Cys Ser Arg Leu Arg Thr Phe Pro Asp Ile Ser Thr His Ile
        835                 840                 845

Thr His Leu Tyr Leu Ser Gly Thr Gly Ile Glu Glu Ile Pro Cys Ser
        850                 855                 860

Ile Glu Lys Phe Ser Arg Leu Gly Ser Leu His Met Asn Gly Cys Asn
865                 870                 875                 880

Asn Leu Glu Tyr Val Asn Leu Asn Leu Phe Lys Leu Lys His Leu His
```

```
                885                 890                 895
Glu Val Asp Phe Ser Asp Cys Lys Cys Leu Asn Leu Asp Gln Glu Ala
            900                 905                 910

Leu Phe Gln Lys Lys Thr Tyr Ser Val Cys Gln Leu Lys Leu Ser Gly
            915                 920                 925

Glu Glu Val Pro Ser Tyr Phe Thr His Arg Thr Gly Thr Ser Ser
    930                 935                 940

Ser Leu Thr Ile Pro Leu Leu His Ser Cys Ile Ser Gln Ser Phe Leu
945                 950                 955                 960

Arg Phe Arg Ala Cys Ile Val Phe Asp Ser Asp Lys Asp Asn Glu Ser
                965                 970                 975

Tyr Ser Arg Cys Ala Phe Arg Phe Lys Gly Ser Phe Arg Asn Cys Ser
            980                 985                 990

Asp Ser Tyr Asn Gln Ala Gln Asp Phe Cys Ala Val Thr Asp Asp Tyr
            995                 1000                1005

Lys Ile Arg Ser Tyr Lys Lys Asp Gly Cys Leu Leu Val Leu Asp
    1010                1015                1020

Tyr Gln Met Ser Gln Ile Pro Leu Glu Met Asn Phe Asp Gly Leu
    1025                1030                1035

Asp Leu Lys Ile His Ile Asp Tyr Cys Arg Ser Ala Lys Ile Lys
    1040                1045                1050

Gly Trp Gly Ile Arg Ile Leu Glu Glu Asp Cys Ser Ser Ala Asp
    1055                1060                1065

Asn Arg Leu Gly Tyr Pro Asn Ile Leu Pro His Val Phe Glu Ala
    1070                1075                1080

Asp Glu Cys Asn Glu Ala Asp Phe Val Asn Lys Leu Leu Ile Val
    1085                1090                1095

Leu Gly Cys Asn Ala Glu His Leu Lys Leu Gly Ile Lys Arg Asp
    1100                1105                1110

Ser His Pro Thr Cys Leu Trp Ile Leu Val Cys Gly Glu Ala Val
    1115                1120                1125

Pro Leu Phe Leu Ser Glu Ile Ala Pro Ala Gln Leu Arg Gly Gly
    1130                1135                1140

Leu Asn Ile Val Phe Gln Leu Met Val Thr Ile Gly Ile Leu Ile
    1145                1150                1155

Ala Asn Leu Val Asn Tyr Phe Thr Ala Thr Val His Pro Asn Gly
    1160                1165                1170

Trp Arg Ile Ala Leu Gly Gly Ala Ala Ile Pro Thr Val Ile Leu
    1175                1180                1185

Val Phe Gly Ser Leu Ile Ile Cys Glu Thr Pro Thr Ser Phe Ile
    1190                1195                1200

Glu Arg Lys Cys
    1205

<210> SEQ ID NO 4
<211> LENGTH: 3729
<212> TYPE: DNA
<213> ORGANISM: Brassica napus

<400> SEQUENCE: 4
atggctctct cattagcttc ttctccttcc tcttctcgca cttggttgta cgatgttttc      60
cctagcttca gtggggtaga cgtccgtgtt actttcctca gccacttgtt gaaggagttt     120
gacaaaaagt tgatcactgc tttcaaagac aacgagatcg agagaagtcg atcactggat     180
```

```
cccgagctta aacaagccat taaagattcg aggatcgcgg tggttatctt ctcccaaaac   240
tatgcctctt caagctggtg tcttaatgag ttgttagaga tagtcaagcg tggtcaaatg   300
gtgataccty ttttctaccg gttggatcct tcccacgtga ggaaacaaac cggtgacttc   360
gggaaaatat ttgaagaaac atgcaagaat caaaagagg aagtgataat aattcaatgg    420
aggagagctt tgaccgatgt agccaataca ctcgggtatc attcagtaaa ctggggtaac   480
gaagctgcaa tgattgaaga aatcgccaat gatgttttgg ataaactact tttaacttca   540
tcgaaggatt cagagaactt tgtgggcatc gaagatcata tcgcagaact gagtgtactg   600
ttgcagttgg acgcgagga agtgaggatg gttggtttat ggggttcctc agggatcggc    660
aagactacaa ttgcaagagt tctgtttcaa cgactttctc gacacttccg aggtagcatt   720
ttcatagaca gggctttcgt atctaagact atggaaattt tcaaggcagc taatccggac   780
gactataaca tgaagctgca tttgcaaaga aatttcctat ctgaaatctt aggtaaagga   840
gacataaaga taaatcattt gagtgcagtt ggggagaggc tgaagaatca gaaagttctt   900
attttcattg atgattttga tgatcaagtt gtgctagaag ccttggttgg tcaaactcaa   960
tggtttggaa gtgggagcag aatcgttgtg gttacaaatg ataagcagta tctaagggcc  1020
catgggatta atcacattta cgaggtctgt ctcccaactg gaaacctagc tgttgagatg  1080
ttatgtcgat atgctttcag gaaaaaggct gcacctgaag gttttgagga gcttgtagct  1140
aaagttacag gacttgctgg tagtcttcct ttaggtctta atgttttggg ttcatctcta  1200
cggggaaggg acaaggagta ctggatggat ttgttgccaa ggcttcggaa ttgtttagat  1260
gggaaaattg agaagacatt gagagtcagc tacgatggat taacaagcga agaagataaa  1320
gccttatttc gccatatcgc atgcctttc aatggtgcaa cagtcacata cctgaagttg   1380
gtgctcactg atagtgggtt gagtgttaat gtggggctgg aaaacctagc tgataagtcc  1440
ctcattcatg aaagagagga ttatgtggag atgcaccgtt tgttagaaga gatgggtaga  1500
cgtattgtta ggcttgagga gcctgaaaaa cgagaatttc tggtggacgc acaagatatc  1560
tgtgatgtac tcagtcaaga cactggtact cataagatat gggtataaa attgaatatt   1620
gatgagattg atgaactgaa tgtgcatgag aatgccttca aagggatgcg caatctgcgt  1680
ttcctggaaa ttcactcaaa aaagcgttat gtgtttggaa aggaagaagt accaattcac  1740
ttacctgaaa acttcgacta tttgcctcca aaacttaaaa tattggattg gtatgaatat  1800
ccaatgagat gtctgccttc taagtttcgt cctgaaaaac tcgtcaagct caaaatggtg  1860
aatagcaagc tcgagaagct gtggaaaggg attgtgtcgc ttacatgtct taataagatg  1920
gatatgtcgg catctcaaaa cttgatagaa atgccagatc tttcaaaggc caccaatctg  1980
gagacactta aacttcggaa ttgctatagt ttggtcaagc ttccttcctc tattccacat  2040
cccaacaaac tgacgacatt aaacttgaag aactgtcgaa atctggagac tattccaatt  2100
ggcattagcc tcaaatctct caaaaaccta aatactaaag gatgctcacg gatgaggatt  2160
tttccccaaa tctcaaccag catcgtagat gtcgacatag ccgcaacatc cattgaagaa  2220
ataccttcaa atttgagttt gtgtttcgag agtctccata cctttacgat gcacagccca  2280
aagaaactat gggaaagagt gcagcttctt actctcctca cgacgatcat gtctccctct  2340
ttgtggtatc tggatctctc ggataaccca ggcttggtgg agcttccttc ttcatttaag  2400
aatctccata acttgcagat attgaaaatt agtaactgcg taaatctgga aactcttccc  2460
accggaatca acctcggatc tctctggcaa ctagatctca gtggatgctc aaggttgagg  2520
actttttcctg atatctcaac caacatcata gttctcgatc tcagcgaaac agccatcgaa  2580
```

-continued

```
gagattcctt gttggattga gaaattctct aaccttaact cccttaggat gaagggatgc    2640
aacaatttgg aatatgtaaa cctaaacatt tctaaactca aacatcttca gaaagtagac    2700
ttttcagact gcaagtcatt gactggagct agcttgaata atcgtccaag agaaagtgcc    2760
ttgagttatt accacatatg ctacattggt atcgatttca ccaagtgctt aaacttggat    2820
caagaagctc tgtttcaaaa gaaaacatat tttggttgtc atctgaagtt gtcaggtgaa    2880
gaagtgcctt catatttcac tcaccgtact actggaaacct cctcctctct caccattcct    2940
ttacttcaca gctgtctctc acaaccattc ctcctattca gggcttgtat tgtgtttgat    3000
tcggacaagg agacatatag cgattgtgtc tttagattca aaggcagttt tcggaactgc    3060
tctgattcct ataatcaggc acaagacttc tgcgcagtca cggatgatta tgagatcaat    3120
tcatatgaga aggatggttg tctgtttgta ttagactacc agatgtctca aatcccttta    3180
gaaatgaact tcgatcgcct ggatctgaag attcatattg ttgattgttt taatgatgct    3240
aaaataaaag gatggggtat acgaatctta gaggaggact gttcatcggc agacaaccga    3300
cttggttatc caaacattct accacatgtt tttgaagccg atgaatgcaa tatgaggctg    3360
gtgaatgtgg aggcaaatga tgcagtgacg gaaagaagcg gtatgcggag aagtaagagc    3420
acaatattgt gggaaggagt agtgcatgca gtgcctcttt ttctatcaga gattgctcct    3480
gcacagctca ggggaggtct caacattgta ttccaactca tggtaacaat tggaatccta    3540
atagccaacc ttgtcaacta cttcactgcc accgttcacc ctaacggatg gcgaatcgcc    3600
ctcggtggag ctgcaatccc cgcggttatc ctcctcttgg gttcactgat catctgtgag    3660 accccccacga gcctcataga gcgcaacaaa aacgaagaag gcagagaaac tctaaggaaa    3720
atcagagga                                                            3729
```

<210> SEQ ID NO 5
<211> LENGTH: 4492
<212> TYPE: DNA
<213> ORGANISM: Brassica napus

<400> SEQUENCE: 5

```
atggctctct cattagcttc ttctccttcc tcttctcgca cttggttgta cgatgttttc     60
cctagcttca gtggggtaga cgtccgtgtt actttcctca gccacttgtt gaaggagttt    120
gacaaaaagt tgatcactgc tttcaaagac aacgagatcg agagaagtcg atcactggat    180
cccgagctta acaagccat  taaagattcg aggatcgcgg tggttatctt ctcccaaaac    240
tatgcctctt caagctggtg tcttaatgag ttgttagaga tagtcaagcg tggtcaaatg    300
gtgatacctg ttttctaccg gttggatcct tcccacgtga ggaaacaaac cggtgacttc    360
gggaaaatat ttgaagaaac atgcaagaat caaaaagagg aagtgataat aattcaatgg    420
aggagagctt tgaccgatgt agccaataca ctcgggtatc attcagtaaa ctggtacggt    480
tttatgcatc attcattctt ttgagtaaag gttagacttc tggttgctag ggggtgtat     540 tatatttctt aatgttaggg gtaacgaagc tgcaatgatt gaagaaatcg ccaatgatgt    600
tttggataaa ctacttttaa cttcatcgaa ggattcagag aactttgtgg gcatcgaaga    660
tcatatcgca gaactgagtg tactgttgca gttggacgcg gaggaagtga ggatggttgg    720 tttatgggt tcctcaggga tcggcaagac tacaattgca agagttctgt ttcaacgact    780
ttctcgacac ttccgaggta gcattttcat agacagggct ttcgtatcta agactatgga    840
aattttcaag gcagctaatc cggacgacta taacatgaag ctgcatttgc aaagaaattt    900
```

```
cctatctgaa atcttaggta aaggagacat aaagataaat catttgagtg cagttgggga    960
gaggctgaag aatcagaaag ttcttatttt cattgatgat tttgatgatc aagttgtgct   1020
agaagccttg gttggtcaaa ctcaatggtt tggaagtggg agcagaatcg ttgtggttac   1080
aaatgataag cagtatctaa gggcccatgg gattaatcac atttacgagg tctgtctccc   1140
aactggaaac ctagctgttg agatgttatg tcgatatgct ttcaggaaaa aggctgcacc   1200
tgaaggtttt gaggagcttg tagctaaagt tacaggactt gctggtagtc ttcctttagg   1260
tcttaatgtt ttgggttcat ctctacgggg aagggacaag gagtactgga tggatttgtt   1320
gccaaggctt cggaattgtt tagatgggaa aattgagaag acattgagag tcagctacga   1380
tggattaaca agcgaagaag ataaagcctt atttcgccat atcgcatgcc ttttcaatgg   1440
tgcaacagtc acatacctga agttggtgct cactgatagt gggttgagtg ttaatgtggg   1500
gctggaaaac ctagctgata agtccctcat tcatgaaaga gaggattatg tggagatgca   1560
ccgtttgtta aagagatgg gtagacgtat tgttaggctt gaggagcctg aaaaacgaga   1620
atttctggtg gacgcacaag atatctgtga tgtactcagt caagcactg taagttatct   1680
cttatgttcg tgctcctttc agtcaataaa taagatttag agcatgccat tttataagca   1740
aaactaatac ttgatattat ataattttca gggtactcat aagatattgg gtataaaatt   1800
gaatattgat gagattgatg aactgaatgt gcatgagaat gccttcaaag ggatgcgcaa   1860
tctgcgtttc ctggaaattc actcaaaaaa gcgttatgtg tttggaaagg aagaagtacc   1920
aattcactta cctgaaaact tcgactattt gcctccaaaa cttaaaatat tggattggta   1980
tgaatatcca atgagatgtc tgccttctaa gtttcgtcct gaaaaactcg tcaagctcaa   2040
aatggtgaat agcaagctcg agaagctgtg gaaagggatt gtggtaagtt ttgagaatag   2100
tttgtgatgt tattagtagt aagactaatc ttgattttat ttttggatg acaatcttgt   2160
tctactgagc tcatgtgttt tgttcctttt tatttgtttt gttgagtaca gtcgcttaca   2220
tgtcttaata agatggatat gtcggcatct caaaacttga tagaaatgcc agatctttca   2280
aaggccacca atctggagac acttaaactt cggaattgct atagtttggt caagcttcct   2340
tcctctattc cacatcccaa caaactgacg acattaaact tgaagaactg tcgaaatctg   2400
gagactattc caattggcat tagcctcaaa tctctcaaaa acctaaatac taaaggatgc   2460
tcacggatga ggattttttcc ccaaatctca accagcatcg tagatgtcga catagccgca   2520
acatccattg aagaaatacc ttcaaatttg agtttgtgtt tcgagagtct ccataccttt   2580
acgatgcaca gcccaaagaa actatgggaa agagtgcagg tatgtatgta gttccaaact   2640
ttgtgtgttt ctccaatctg ttttacgtta tagatattag ataatggtgc aaatgaaact   2700
aaggttatat tgtatttatc ggagggaaga agagtagcgc tgaatatgat tttgtgtatt   2760
tggttcagct tcttactctc ctcacgacga tcatgtctcc ctctttgtgg tatctggatc   2820
tctcggataa cccaggcttg gtggagcttc cttcttcatt taagaatctc cataacttgc   2880
agatattgaa aattagtaac tgcgtaaatc tggaaactct tccccaccgga atcaacctcg   2940
gatctctctg gcaactagat ctcagtggat gctcaaggtt gaggactttt cctgatatct   3000
caaccaacat catagttctc gatctcagcg aaacagccat cgaagagatt ccttgttgga   3060
ttgagaaatt ctctaacctt aactccctta ggatgaaggg atgcaacaat ttggaatatg   3120
taaacctaaa catttctaaa ctcaaacatc ttcagaaagt agacttttca gactgcaagt   3180
cattgactgg agctagcttg aataatcgtc aagagaaag tgccttgagt tattaccaca   3240
tatgctacat tggtatcgat ttcaccaagt gcttaaactt ggatcaagaa gctctgtttc   3300
```

-continued

```
aaaagaaaac atattttggt tgtcatctga agttgtcagg tgaagaagtg ccttcatatt    3360
tcactcaccg tactactgga acctcctcct ctctcaccat tcctttactt cacagctgtc    3420
tctcacaacc attcctccta ttcagggctt gtattgtgtt tgattcggac aaggagacat    3480
atagcgattg tgtctttaga ttcaaaggca gttttcggaa ctgctctgat tcctataatc    3540
aggcacaaga cttctgcgca gtcacggatg attatgagat caattcatat gagaaggatg    3600
gttgtctgtt tgtattagac taccagatgt ctcaaatccc tttagaaatg aacttcgatc    3660
gcctggatct gaagattcat attgttgatt gttttaatga tgctaaaata aaaggatggg    3720
gtatacgaat cttagaggag gactgttcat cggcagacaa ccgacttggt tatccaaaca    3780
ttctaccaca tgttttgaa gccgatgaat gcaatatgag gctggtgaat gtggaggcaa    3840
atgatgcagt gacggaaaga agcgggtaaa gggcattaat catgaactta tcacagtatt    3900
ttctatatca taatttcttg tactgagact ttttttttct ttttctgcag atttcgtgaa    3960 taaagtttg attgtgttag gttgtaacgc agagcatcta aaattaggaa ttaagagagt    4020
ttcccatcca acttgcttgt ggatcttagt atgcggagaa gtaagagcac aatattgtgg    4080
gaaggagtag tgcatgtatg ttttcttcaa ccttccttcc tttatactag ttcttacaaa    4140
aatggttatg cctggcagat ctctagaaat gacctaactt tattgtgtgt accttaaatt    4200
ctcaggcagt gcctcttttt ctatcagaga ttgctcctgc acagctcagg ggaggtctca    4260
acattgtatt ccaactcatg gtaacaattg gaatcctaat agccaacctt gtcaactact    4320
tcactgccac cgttcaccct aacggatggc gaatcgccct cggtggagct gcaatccccg    4380
cggttatcct cctcttgggt tcactgatca tctgtgagac ccccacgagc ctcatagagc    4440
gcaacaaaaa cgaagaaggc agagaaactc taaggaaaat cagaggagtt ga            4492
```

<210> SEQ ID NO 6
<211> LENGTH: 1243
<212> TYPE: PRT
<213> ORGANISM: Brassica napus

<400> SEQUENCE: 6

```
Met Ala Leu Ser Leu Ala Ser Ser Pro Ser Ser Arg Thr Trp Leu
1               5                   10                  15

Tyr Asp Val Phe Pro Ser Phe Ser Gly Val Asp Val Arg Val Thr Phe
                20                  25                  30

Leu Ser His Leu Leu Lys Glu Phe Asp Lys Lys Leu Ile Thr Ala Phe
            35                  40                  45

Lys Asp Asn Glu Ile Glu Arg Ser Arg Ser Leu Asp Pro Glu Leu Lys
        50                  55                  60

Gln Ala Ile Lys Asp Ser Arg Ile Ala Val Val Ile Phe Ser Gln Asn
65                  70                  75                  80

Tyr Ala Ser Ser Ser Trp Cys Leu Asn Glu Leu Leu Glu Ile Val Lys
                85                  90                  95

Arg Gly Gln Met Val Ile Pro Val Phe Tyr Arg Leu Asp Pro Ser His
                100                 105                 110

Val Arg Lys Gln Thr Gly Asp Phe Gly Lys Ile Phe Glu Glu Thr Cys
            115                 120                 125

Lys Asn Gln Lys Glu Glu Val Ile Ile Ile Gln Trp Arg Arg Ala Leu
        130                 135                 140

Thr Asp Val Ala Asn Thr Leu Gly Tyr His Ser Val Asn Trp Gly Asn
145                 150                 155                 160
```

```
Glu Ala Ala Met Ile Glu Glu Ile Ala Asn Asp Val Leu Asp Lys Leu
            165                 170                 175

Leu Leu Thr Ser Ser Lys Asp Ser Glu Asn Phe Val Gly Ile Glu Asp
        180                 185                 190

His Ile Ala Glu Leu Ser Val Leu Leu Gln Leu Asp Ala Glu Glu Val
            195                 200                 205

Arg Met Val Gly Leu Trp Gly Ser Ser Gly Ile Gly Lys Thr Thr Ile
        210                 215                 220

Ala Arg Val Leu Phe Gln Arg Leu Ser Arg His Phe Arg Gly Ser Ile
225                 230                 235                 240

Phe Ile Asp Arg Ala Phe Val Ser Lys Thr Met Glu Ile Phe Lys Ala
            245                 250                 255

Ala Asn Pro Asp Asp Tyr Asn Met Lys Leu His Leu Gln Arg Asn Phe
        260                 265                 270

Leu Ser Glu Ile Leu Gly Lys Gly Asp Ile Lys Ile Asn His Leu Ser
    275                 280                 285

Ala Val Gly Glu Arg Leu Lys Asn Gln Lys Val Leu Ile Phe Ile Asp
    290                 295                 300

Asp Phe Asp Asp Gln Val Val Leu Glu Ala Leu Val Gly Gln Thr Gln
305                 310                 315                 320

Trp Phe Gly Ser Gly Ser Arg Ile Val Val Thr Asn Asp Lys Gln
                325                 330                 335

Tyr Leu Arg Ala His Gly Ile Asn His Ile Tyr Glu Val Cys Leu Pro
            340                 345                 350

Thr Gly Asn Leu Ala Val Glu Met Leu Cys Arg Tyr Ala Phe Arg Lys
        355                 360                 365

Lys Ala Ala Pro Glu Gly Phe Glu Glu Leu Val Ala Lys Val Thr Gly
    370                 375                 380

Leu Ala Gly Ser Leu Pro Leu Gly Leu Asn Val Leu Gly Ser Ser Leu
385                 390                 395                 400

Arg Gly Arg Asp Lys Glu Tyr Trp Met Asp Leu Leu Pro Arg Leu Arg
            405                 410                 415

Asn Cys Leu Asp Gly Lys Ile Glu Lys Thr Leu Arg Val Ser Tyr Asp
        420                 425                 430

Gly Leu Thr Ser Glu Glu Asp Lys Ala Leu Phe Arg His Ile Ala Cys
    435                 440                 445

Leu Phe Asn Gly Ala Thr Val Thr Tyr Leu Lys Leu Val Leu Thr Asp
    450                 455                 460

Ser Gly Leu Ser Val Asn Val Gly Leu Glu Asn Leu Ala Asp Lys Ser
465                 470                 475                 480

Leu Ile His Glu Arg Glu Asp Tyr Val Glu Met His Arg Leu Leu Glu
            485                 490                 495

Glu Met Gly Arg Arg Ile Val Arg Leu Glu Glu Pro Glu Lys Arg Glu
        500                 505                 510

Phe Leu Val Asp Ala Gln Asp Ile Cys Asp Val Leu Ser Gln Asp Thr
    515                 520                 525

Gly Thr His Lys Ile Leu Gly Ile Lys Leu Asn Ile Asp Glu Ile Asp
    530                 535                 540

Glu Leu Asn Val His Glu Asn Ala Phe Lys Gly Met Arg Asn Leu Arg
545                 550                 555                 560

Phe Leu Glu Ile His Ser Lys Lys Arg Tyr Val Phe Gly Lys Glu Glu
            565                 570                 575

Val Pro Ile His Leu Pro Glu Asn Phe Asp Tyr Leu Pro Pro Lys Leu
```

-continued

```
                580                 585                 590
Lys Ile Leu Asp Trp Tyr Glu Tyr Pro Met Arg Cys Leu Pro Ser Lys
                    595                 600                 605

Phe Arg Pro Glu Lys Leu Val Lys Leu Lys Met Val Asn Ser Lys Leu
            610                 615                 620

Glu Lys Leu Trp Lys Gly Ile Val Ser Leu Thr Cys Leu Asn Lys Met
625                 630                 635                 640

Asp Met Ser Ala Ser Gln Asn Leu Ile Glu Met Pro Asp Leu Ser Lys
                    645                 650                 655

Ala Thr Asn Leu Glu Thr Leu Lys Leu Arg Asn Cys Tyr Ser Leu Val
                660                 665                 670

Lys Leu Pro Ser Ser Ile Pro His Pro Asn Lys Leu Thr Thr Leu Asn
            675                 680                 685

Leu Lys Asn Cys Arg Asn Leu Glu Thr Ile Pro Ile Gly Ile Ser Leu
        690                 695                 700

Lys Ser Leu Lys Asn Leu Asn Thr Lys Gly Cys Ser Arg Met Arg Ile
705                 710                 715                 720

Phe Pro Gln Ile Ser Thr Ser Ile Val Asp Val Asp Ile Ala Ala Thr
                    725                 730                 735

Ser Ile Glu Glu Ile Pro Ser Asn Leu Ser Leu Cys Phe Glu Ser Leu
                740                 745                 750

His Thr Phe Thr Met His Ser Pro Lys Lys Leu Trp Glu Arg Val Gln
            755                 760                 765

Leu Leu Thr Leu Leu Thr Thr Ile Met Ser Pro Ser Leu Trp Tyr Leu
        770                 775                 780

Asp Leu Ser Asp Asn Pro Gly Leu Val Glu Leu Pro Ser Ser Phe Lys
785                 790                 795                 800

Asn Leu His Asn Leu Gln Ile Leu Lys Ile Ser Asn Cys Val Asn Leu
                    805                 810                 815

Glu Thr Leu Pro Thr Gly Ile Asn Leu Gly Ser Leu Trp Gln Leu Asp
                820                 825                 830

Leu Ser Gly Cys Ser Arg Leu Arg Thr Phe Pro Asp Ile Ser Thr Asn
            835                 840                 845

Ile Ile Val Leu Asp Leu Ser Glu Thr Ala Ile Glu Glu Ile Pro Cys
        850                 855                 860

Trp Ile Glu Lys Phe Ser Asn Leu Asn Ser Leu Arg Met Lys Gly Cys
865                 870                 875                 880

Asn Asn Leu Glu Tyr Val Asn Leu Asn Ile Ser Lys Leu Lys His Leu
                    885                 890                 895

Gln Lys Val Asp Phe Ser Asp Cys Lys Ser Leu Thr Gly Ala Ser Leu
                900                 905                 910

Asn Asn Arg Pro Arg Glu Ser Ala Leu Ser Tyr Tyr His Ile Cys Tyr
            915                 920                 925

Ile Gly Ile Asp Phe Thr Lys Cys Leu Asn Leu Asp Gln Glu Ala Leu
        930                 935                 940

Phe Gln Lys Lys Thr Tyr Phe Gly Cys His Leu Lys Leu Ser Gly Glu
945                 950                 955                 960

Glu Val Pro Ser Tyr Phe Thr His Arg Thr Thr Gly Ser Ser Ser
                    965                 970                 975

Leu Thr Ile Pro Leu Leu His Ser Cys Leu Ser Gln Pro Phe Leu Leu
                980                 985                 990

Phe Arg Ala Cys Ile Val Phe Asp  Ser Asp Lys Glu Thr  Tyr Ser Asp
            995                 1000                1005
```

| | | | | | | | | | |
|---|---|---|---|---|---|---|---|---|---|
| Cys | Val | Phe | Arg | Phe | Lys | Gly | Ser | Phe | Arg | Asn | Cys | Ser | Asp | Ser |
| | 1010 | | | | 1015 | | | | 1020 | | | | | |

Cys Val Phe Arg Phe Lys Gly Ser Phe Arg Asn Cys Ser Asp Ser
    1010                1015                1020

Tyr Asn Gln Ala Gln Asp Phe Cys Ala Val Thr Asp Asp Tyr Glu
    1025                1030                1035

Ile Asn Ser Tyr Glu Lys Asp Gly Cys Leu Phe Val Leu Asp Tyr
    1040                1045                1050

Gln Met Ser Gln Ile Pro Leu Glu Met Asn Phe Asp Arg Leu Asp
    1055                1060                1065

Leu Lys Ile His Ile Val Asp Cys Phe Asn Asp Ala Lys Ile Lys
    1070                1075                1080

Gly Trp Gly Ile Arg Ile Leu Glu Glu Asp Cys Ser Ser Ala Asp
    1085                1090                1095

Asn Arg Leu Gly Tyr Pro Asn Ile Leu Pro His Val Phe Glu Ala
    1100                1105                1110

Asp Glu Cys Asn Met Arg Leu Val Asn Val Glu Ala Asn Asp Ala
    1115                1120                1125

Val Thr Glu Arg Ser Gly Met Arg Arg Ser Lys Ser Thr Ile Leu
    1130                1135                1140

Trp Glu Gly Val Val His Ala Val Pro Leu Phe Leu Ser Glu Ile
    1145                1150                1155

Ala Pro Ala Gln Leu Arg Gly Gly Leu Asn Ile Val Phe Gln Leu
    1160                1165                1170

Met Val Thr Ile Gly Ile Leu Ile Ala Asn Leu Val Asn Tyr Phe
    1175                1180                1185

Thr Ala Thr Val His Pro Asn Gly Trp Arg Ile Ala Leu Gly Gly
    1190                1195                1200

Ala Ala Ile Pro Ala Val Ile Leu Leu Leu Gly Ser Leu Ile Ile
    1205                1210                1215

Cys Glu Thr Pro Thr Ser Leu Ile Glu Arg Asn Lys Asn Glu Glu
    1220                1225                1230

Gly Arg Glu Thr Leu Arg Lys Ile Arg Gly
    1235                1240

<210> SEQ ID NO 7
<211> LENGTH: 3585
<212> TYPE: DNA
<213> ORGANISM: Brassica napus

<400> SEQUENCE: 7

```
atggctctct cattagcttc ttctccttcc tcttctcgca cttggttgta cgatgttttc      60
cctagcttca gtgggtaga  cgttcgtgtt actttcctca gccacttgtt gaaggagttt     120
gacaaaaagt tgatcactgc tttcaaagac aacgagatcg agagaagtcg atcactggat     180
cccgagctca acaagccat  taagattcg  aggatcgcag tggttatctt ctcccaaaac     240
tatgcctctt caagctggtg tcttaatgag ttgttagaga tagtcaagcg tggtcaaatg     300
gtgataccty ttttctaccg gttggatcct tcccacgtga ggaaacaaac cggtgaattt     360
gggaaaatat tgaagaaac  atgcaagaat caaaagagg  aagtgataat aactcaatgg     420
aggagagctt tgaccgatgt agccaatact ctcgggtatc attcggtaaa ctggggtaac     480
gaagctgcaa tgattgaaga atcgccaat  gatgttttgg ataaactact tttaacttca     540
tcgaaggatt cagagaactt tgtgggcatc gaagatcatc ttgcagaact gagtgtattg     600
ctgcagttgg acgcggagga agtgaggatg gttggtttat ggggttcctc agggatcggc     660
```

```
aagactacaa ttgcaagagt tctgtttcaa cgactttctc gacacttccg aggtagcatt    720
ttcatagaca gggctttcgt atctaagact atggaaattt tcaaggaagc taatccggac    780
gactataaca tgaagctgca tttgcaaaga aatttcctat ctgaaatctt aggtaaagga    840
gacataaaga taaatcattt gagtgcagtt gaagagaggc tgaagaatca gaaagttctt    900
attttcattg atgattttga tgatcaagtt gtgctagaag ccttggttgg tcaaactcaa    960
tggtttggaa gtgggagcag aatcgttgtg gttacaaatg ataagcagta tctaagggcc   1020
catgggatta atcacattta cgaggtctgt ctcccaactg aaaacctagc tgttgagatg   1080
ttatgtcgat ctgctttcag gaaaaaggct gcacctgaag ttttgaggga gcttgtagct   1140
aaagttacag gacttgctgg tagtcttcct ttaggtctta atgttttggg ttcatatcta   1200
cggggaaggg agaagaagta ctggatggat ttgttgccaa ggcttcagaa tggtttagat   1260
gggaaaattg agaagacatt gagggtcagc tacgatggat aacaagcga agaagataaa    1320 gcgttatttc gccatatcgc atgccttttc caatggaaaa aagtcacata cctgaagttg   1380
ctgctcgctg atagtgggtt gagtgttacg gttgggctgg aaaacctagc tgataagtcc   1440
atcattcatg taagtacgaa ttatgtggtg atgcaccgtt tgttagaaga tgggtaga    1500 ggtattgtta ggcttgacga gcctgaaaaa cgagaatttc tggtggacgc acaagatatc   1560
tgtgatgtac tcagtcaaga cactggtact cataagatat tgggtataaa attgaatatt   1620
gatgagattg atgaactgaa tgtgcatgag aatgccttca aagggatgcg caatctgcgt   1680
ttcctggaaa ttcactcaca aaaccgtcat gagtttggaa acgaagaagt tagaattcac   1740
ttacctgaaa acttcgacta tttgcctcca aaacttaaaa tattggattg gtttggatat   1800
ccaatgagat gtctgccttc taagtttcgt cctgaaaaac tcgtcaagct caaaatggtg   1860
aatagcaagc tcgagaagct gtgggaaggg attgtgtcgc ttacatgtct taagagatg    1920 gatatgtcgg gatctacaaa cttgatagaa atgccagatc tttcaaaggc caccaatctg   1980
gagacactta atgttgggc ttgctatagt ttggtgactt tccccaaat ctcaagcacc     2040 atcgtagatg tcgacatagc cggaacatcc attgaagaaa taccttcaaa tttgagtttg   2100
tgtttcgaga atctccatac ctttaagatg cacagcccaa agaaactatc ggaaagagtg   2160
cagcttctta ctctcctcac gccgatcatg tctccctctt tgtggtatct gaatctctcg   2220
gataaccctg gctggtgga gcttccttct tcatttaaga atctccataa actggagaga    2280
ttgaaaatta gaaactgcgt aaatctggaa actcttccca ccggaatcaa cctcggatct   2340
ctctcgagag tagatctaag gggatgctca cggttgagaa cttttcctga tatctcaacc   2400
aacatcaaaa acctcgatct cagcgaaaca gccattgaag agattccttg ttggattgag   2460
aaattctcca ggctttactc cctacgatg aagggatgca acaatttgga atatgtaaac    2520
ctaaacattt ctaaactcaa atatcttttc gaagtcgact tttcagactg caagtcattg   2580
actggagcta gctggaataa tcgtccaaga gaaagtgcct tgagttatta ccacagtttc   2640
gacattggta tcgatttcac caagtgctta aacttggatc aagaagctct gtttcaaaag   2700
aaaacatatt tcggttgtca actgaagttg tcaggtgaag aagtgccttc atatttcacg   2760
caccgtacta ctggaacctc ctcctctctc accattcctt tacttcacag ctgtctctca   2820
caaccattcc tccgattcag ggcttgcatt gtgtttgatt cgcacaatga gacatatagc   2880
aaatgtgtct ttagattcaa aggcagtttt cagaactgct ctgattccta taatcaggca   2940
caagacttct cgcgcagtca cggaggattat ttgatctatt catatgagaa ggatggttgt   3000
ctgtttgtat tagactacca gatgtctcaa atcccttag aaatgaactt cgatggcctg    3060
```

```
gatctgaaga ttcatattgt tgattgttat aatgctaaaa taaaaggatg gggtatacga    3120
atcttagagg aggactgttc atcggcagac aaccgacttg gttatccaaa cattctacca    3180 catgttttg aagccgatga atgcaatatg aggctggtga atgtggaggc aaatgatgca     3240
gtgacggaaa aagcggtat gcggagaagt aagagcacaa tattgtggga aggagtagtg     3300
catgcagtgc ctcttttct atcagagatt gttcctgcac agctcaaggg aggtctcaac     3360
attgtattcc aactcatggt cacaattgga atcctaatag ccaacctggt caactacttc    3420
actgccaccg ttcaccctaa cggatcgcga atcgccctcg gtggagctgc aatccccgcg    3480
gttatcctcc tcttgggttc actgatcatc tgtgagaccc ccacgagcct catagagcgc    3540
aacaaaaacg aagaaggcag agaaactcta aggaagatca gagga                   3585

<210> SEQ ID NO 8
<211> LENGTH: 4344
<212> TYPE: DNA
<213> ORGANISM: Brassica napus

<400> SEQUENCE: 8
atggctctct cattagcttc ttctccttcc tcttctcgca cttggttgta cgatgttttc      60
cctagcttca gtggggtaga cgttcgtgtt actttcctca gccacttgtt gaaggagttt     120
gacaaaaagt tgatcactgc tttcaaagac aacgagatcg agagaagtcg atcactggat     180
cccgagctca acaagccat taagattcg aggatcgcag tggttatctt ctcccaaaac       240
tatgcctctt caagctggtg tcttaatgag ttgttagaga tagtcaagcg tggtcaaatg     300
gtgatacctg ttttctaccg gttggatcct tcccacgtga ggaaacaaac cggtgaattt     360
gggaaaatat ttgaagaaac atgcaagaat caaaagagg aagtgataat aactcaatgg      420
aggagagctt tgaccgatgt agccaatact ctcgggtatc attcggtaaa ctggtacggt     480
tttatgcatc attcattctt ttgagtaaag gttagacttc tggttgcttg ggggtgatat     540
tatctttctt attgttaggg gtaacgaagc tgcaatgatt gaagaaatcg ccaatgatgt     600
tttggataaa ctacttttaa cttcatcgaa ggattcagag aactttgtgg gcatcgaaga     660
tcatcttgca gaactgagtg tattgctgca gttggacgcg gaggaagtga ggatggttgg     720
tttatggggt tcctcaggga tcggcaagac tacaattgca agagttctgt ttcaacgact     780
ttctcgacac ttccgaggta gcattttcat agacagggct ttcgtatcta agactatgga     840
aattttcaag gaagctaatc cggacgacta taacatgaag ctgcatttgc aaagaaattt     900
cctatctgaa atcttaggta aaggagacat aaagataaat catttgagtg cagttgaaga     960
gaggctgaag aatcagaaag ttcttatttt cattgatgat tttgatgatc aagttgtgct    1020
agaagccttg gttggtcaaa ctcaatggtt tggaagtggg agcagaatcg ttgtggttac    1080
aaatgataag cagtatctaa gggcccatgg gattaatcac atttacgagg tctgtctccc    1140
aactgaaaac ctagctgttg agatgttatg tcgatctgct ttcaggaaaa aggctgcacc    1200
tgaaggtttt gaggagcttg tagctaaagt tacaggactt gctggtagtc ttcctttagg    1260
tcttaatgtt ttgggttcat atctacgggg aaggagaag aagtactgga tggatttgtt     1320
gccaaggctt cagaatggtt tagatgggaa aattgagaag acattgaggg tcagctacga    1380
tggattaaca agcgaagaag ataaagcgtt atttcgccat atcgcatgcc ttttccaatg    1440
gaaaaaagtc acatacctga agttgctgct cgctgatagt gggttgagtg ttacggttgg    1500
gctggaaaac ctagctgata agtccatcat tcatgtaagt acgaattatg tggtgatgca    1560
```

-continued

```
ccgtttgtta gaagagatgg gtagaggtat tgttaggctt gacgagcctg aaaaacgaga    1620
atttctggtg gacgcacaag atatctgtga tgtactcagt caagacactg taagttatct    1680
cttatgttcg tgctccttac agtcaataaa taagatttag agcatgccat tttataagca    1740
aaactaatac ttgatattat ataattttca gggtactcat aagatattgg gtataaaatt    1800
gaatattgat gagattgatg aactgaatgt gcatgagaat gccttcaaag ggatgcgcaa    1860
tctgcgtttc ctggaaattc actcacaaaa ccgtcatgag tttggaaacg aagaagttag    1920
aattcactta cctgaaaact tcgactattt gcctccaaaa cttaaaatat tggattggtt    1980
tggatatcca atgagatgtc tgccttctaa gtttcgtcct gaaaaactcg tcaagctcaa    2040
aatggtgaat agcaagctcg agaagctgtg ggaagggatt gtggtaagtt ttgagaatag    2100
tttgtgatgt tatttgtagt aagactaatc tttatttat ttttttggatg acaatcttgt    2160 tctactgagc tcatgtgttc tgttcctttt ttttttttgtt gagtacagtc gcttacatgt    2220
cttaaagaga tggatatgtc gggatctaca aacttgatag aaatgccaga tctttcaaag    2280
gccaccaatc tggagacact taatgttggg gcttgctata gtttggtgac ttttcccccaa    2340 atctcaagca ccatcgtaga tgtcgacata gccggaacat ccattgaaga aataccttca    2400
aatttgagtt tgtgtttcga gaatctccat acctttaaga tgcacagccc aaagaaacta    2460
tcggaaagag tgcaggtatg tatgtagttc caaactttgt gtgtttctcc aatctgtttt    2520
acgttataga tattagatat tggtgaaaat gaaactaagg ttatattgta tttatcggag    2580
ggaagaagag tagcgctgaa tatgattttg tgtatttggt tcagcttctt actctcctca    2640
cgccgatcat gtctccctct ttgtggtatc tgaatctctc ggataaccct ggcttggtgg    2700
agcttccttc ttcatttaag aatctccata aactggagag attgaaaatt agaaactgcg    2760
taaatctgga aactcttccc accggaatca acctcggatc tctctcgaga gtagatctaa    2820
ggggatgctc acggttgaga acttttcctg atatctcaac caacatcaaa aacctcgatc    2880
tcagcgaaac agccattgaa gagattcctt gttggattga gaaattctcc aggctttact    2940
ccctacggat gaagggatgc aacaatttgg aatatgtaaa cctaaacatt tctaaactca    3000
aatatctttt cgaagtcgac ttttcagact gcaagtcatt gactggagct agctggaata    3060
atcgtccaag agaaagtgcc ttgagttatt accacagttt cgacattggt atcgatttca    3120
ccaagtgctt aaacttggat caagaagctc tgtttcaaaa gaaaacatat ttcggttgtc    3180
aactgaagtt gtcaggtgaa gaagtgcctt catatttcac gcaccgtact actggaacct    3240
cctcctctct caccattcct ttacttcaca gctgtctctc acaaccattc ctccgattca    3300
gggcttgcat tgtgtttgat tcgcacaatg agacatatag caaatgtgtc tttagattca    3360
aaggcagttt tcagaactgc tctgattcct ataatcaggc acaagacttc tgcgcagtca    3420
cggaggatta tttgatctat tcatatgaga aggatggttg tctgtttgta ttagactacc    3480
agatgtctca aatccctttta gaatgaact tcgatggcct ggatctgaag attcatattg    3540
ttgattgtta taatgctaaa ataaaaggat ggggtatacg aatcttagag gaggactgtt    3600
catcggcaga caaccgactt ggttatccaa acattctacc acatgttttt gaagccgatg    3660
aatgcaatat gaggctggtg aatgtggagg caaatgatgc agtgacggaa agaagcgggt    3720
aaaggcatta atcatgaact tatcacagta ttttctatat cataatttct tgtactgaga    3780
cttttttttc ttttttctgca gatttcgtga ataaagtttt gattgtgtta ggttgtaacg    3840
cagagcatct aaaattagga attaagagag tttcccatcc aacttgcttg tggatcttag    3900
tatgcggaga agtaagagca caatattgtg ggaaggagta gtgcatgtat gttttcttca    3960
```

```
accttccttc cttttatact agttcttaca aaaatggtta tgcctggcag atctctagaa    4020
atgaccaaac attattgtgt gtaccttaaa ttctcaggca gtgcctcttt ttctatcaga    4080
gattgttcct gcacagctca agggaggtct caacattgta ttccaactca tggtcacaat    4140
tggaatccta atagccaacc tggtcaacta cttcactgcc accgttcacc ctaacggatc    4200
gcgaatcgcc ctcggtggag ctgcaatccc cgcggttatc ctcctcttgg gttcactgat    4260
catctgtgag accccacga gcctcataga gcgcaacaaa aacgaagaag cagagaaac     4320 tctaaggaag atcagaggag ttga                                          4344
```

<210> SEQ ID NO 9
<211> LENGTH: 1195
<212> TYPE: PRT
<213> ORGANISM: Brassica napus

<400> SEQUENCE: 9

```
Met Ala Leu Ser Leu Ala Ser Ser Pro Ser Ser Arg Thr Trp Leu
1               5                   10                  15

Tyr Asp Val Phe Pro Ser Phe Ser Gly Val Asp Val Arg Val Thr Phe
                20                  25                  30

Leu Ser His Leu Leu Lys Glu Phe Asp Lys Lys Leu Ile Thr Ala Phe
            35                  40                  45

Lys Asp Asn Glu Ile Glu Arg Ser Arg Ser Leu Asp Pro Glu Leu Lys
        50                  55                  60

Gln Ala Ile Lys Asp Ser Arg Ile Ala Val Val Ile Phe Ser Gln Asn
65                  70                  75                  80

Tyr Ala Ser Ser Ser Trp Cys Leu Asn Glu Leu Leu Glu Ile Val Lys
                85                  90                  95

Arg Gly Gln Met Val Ile Pro Val Phe Tyr Arg Leu Asp Pro Ser His
                100                 105                 110

Val Arg Lys Gln Thr Gly Glu Phe Gly Lys Ile Phe Glu Glu Thr Cys
            115                 120                 125

Lys Asn Gln Lys Glu Glu Val Ile Ile Thr Gln Trp Arg Arg Ala Leu
        130                 135                 140

Thr Asp Val Ala Asn Thr Leu Gly Tyr His Ser Val Asn Trp Gly Asn
145                 150                 155                 160

Glu Ala Ala Met Ile Glu Glu Ile Ala Asn Asp Val Leu Asp Lys Leu
                165                 170                 175

Leu Leu Thr Ser Ser Lys Asp Ser Glu Asn Phe Val Gly Ile Glu Asp
            180                 185                 190

His Leu Ala Glu Leu Ser Val Leu Leu Gln Leu Asp Ala Glu Glu Val
        195                 200                 205

Arg Met Val Gly Leu Trp Gly Ser Ser Gly Ile Gly Lys Thr Thr Ile
    210                 215                 220

Ala Arg Val Leu Phe Gln Arg Leu Ser Arg His Phe Arg Gly Ser Ile
225                 230                 235                 240

Phe Ile Asp Arg Ala Phe Val Ser Lys Thr Met Glu Ile Phe Lys Glu
                245                 250                 255

Ala Asn Pro Asp Asp Tyr Asn Met Lys Leu His Leu Gln Arg Asn Phe
            260                 265                 270

Leu Ser Glu Ile Leu Gly Lys Gly Asp Ile Lys Ile Asn His Leu Ser
        275                 280                 285

Ala Val Glu Glu Arg Leu Lys Asn Gln Lys Val Leu Ile Phe Ile Asp
    290                 295                 300
```

Asp Phe Asp Asp Gln Val Val Leu Glu Ala Leu Val Gly Gln Thr Gln
305                 310                 315                 320

Trp Phe Gly Ser Gly Ser Arg Ile Val Val Thr Asn Asp Lys Gln
            325                 330                 335

Tyr Leu Arg Ala His Gly Ile Asn His Ile Tyr Glu Val Cys Leu Pro
            340                 345                 350

Thr Glu Asn Leu Ala Val Glu Met Leu Cys Arg Ser Ala Phe Arg Lys
            355                 360                 365

Lys Ala Ala Pro Glu Gly Phe Glu Leu Val Ala Lys Val Thr Gly
370                 375                 380

Leu Ala Gly Ser Leu Pro Leu Gly Leu Asn Val Leu Gly Ser Tyr Leu
385                 390                 395                 400

Arg Gly Arg Glu Lys Lys Tyr Trp Met Asp Leu Leu Pro Arg Leu Gln
            405                 410                 415

Asn Gly Leu Asp Gly Lys Ile Glu Lys Thr Leu Arg Val Ser Tyr Asp
            420                 425                 430

Gly Leu Thr Ser Glu Glu Asp Lys Ala Leu Phe Arg His Ile Ala Cys
            435                 440                 445

Leu Phe Gln Trp Lys Lys Val Thr Tyr Leu Lys Leu Leu Leu Ala Asp
    450                 455                 460

Ser Gly Leu Ser Val Thr Val Gly Leu Glu Asn Leu Ala Asp Lys Ser
465                 470                 475                 480

Ile Ile His Val Ser Thr Asn Tyr Val Val Met His Arg Leu Leu Glu
            485                 490                 495

Glu Met Gly Arg Gly Ile Val Arg Leu Asp Glu Pro Glu Lys Arg Glu
            500                 505                 510

Phe Leu Val Asp Ala Gln Asp Ile Cys Asp Val Leu Ser Gln Asp Thr
    515                 520                 525

Gly Thr His Lys Ile Leu Gly Ile Lys Leu Asn Ile Asp Glu Ile Asp
    530                 535                 540

Glu Leu Asn Val His Glu Asn Ala Phe Lys Gly Met Arg Asn Leu Arg
545                 550                 555                 560

Phe Leu Glu Ile His Ser Gln Asn Arg His Glu Phe Gly Asn Glu Glu
            565                 570                 575

Val Arg Ile His Leu Pro Glu Asn Phe Asp Tyr Leu Pro Pro Lys Leu
            580                 585                 590

Lys Ile Leu Asp Trp Phe Gly Tyr Pro Met Arg Cys Leu Pro Ser Lys
    595                 600                 605

Phe Arg Pro Glu Lys Leu Val Lys Leu Lys Met Val Asn Ser Lys Leu
    610                 615                 620

Glu Lys Leu Trp Glu Gly Ile Val Ser Leu Thr Cys Leu Lys Glu Met
625                 630                 635                 640

Asp Met Ser Gly Ser Thr Asn Leu Ile Glu Met Pro Asp Leu Ser Lys
            645                 650                 655

Ala Thr Asn Leu Glu Thr Leu Asn Val Gly Ala Cys Tyr Ser Leu Val
            660                 665                 670

Thr Phe Pro Gln Ile Ser Ser Thr Ile Val Asp Val Asp Ile Ala Gly
    675                 680                 685

Thr Ser Ile Glu Glu Ile Pro Ser Asn Leu Ser Leu Cys Phe Glu Asn
    690                 695                 700

Leu His Thr Phe Lys Met His Ser Pro Lys Lys Leu Ser Glu Arg Val
705                 710                 715                 720

```
Gln Leu Leu Thr Leu Leu Thr Pro Ile Met Ser Pro Ser Leu Trp Tyr
                725                 730                 735

Leu Asn Leu Ser Asp Asn Pro Gly Leu Val Glu Leu Pro Ser Ser Phe
        740                 745                 750

Lys Asn Leu His Lys Leu Glu Arg Leu Lys Ile Arg Asn Cys Val Asn
        755                 760                 765

Leu Glu Thr Leu Pro Thr Gly Ile Asn Leu Gly Ser Leu Ser Arg Val
        770                 775                 780

Asp Leu Arg Gly Cys Ser Arg Leu Arg Thr Phe Pro Asp Ile Ser Thr
785                 790                 795                 800

Asn Ile Lys Asn Leu Asp Leu Ser Glu Thr Ala Ile Glu Glu Ile Pro
                805                 810                 815

Cys Trp Ile Glu Lys Phe Ser Arg Leu Tyr Ser Leu Arg Met Lys Gly
                820                 825                 830

Cys Asn Asn Leu Glu Tyr Val Asn Leu Asn Ile Ser Lys Leu Lys Tyr
                835                 840                 845

Leu Phe Glu Val Asp Phe Ser Asp Cys Lys Ser Leu Thr Gly Ala Ser
        850                 855                 860

Trp Asn Asn Arg Pro Arg Glu Ser Ala Leu Ser Tyr Tyr His Ser Phe
865                 870                 875                 880

Asp Ile Gly Ile Asp Phe Thr Lys Cys Leu Asn Leu Asp Gln Glu Ala
                885                 890                 895

Leu Phe Gln Lys Lys Thr Tyr Phe Gly Cys Gln Leu Lys Leu Ser Gly
                900                 905                 910

Glu Glu Val Pro Ser Tyr Phe Thr His Arg Thr Thr Gly Thr Ser Ser
                915                 920                 925

Ser Leu Thr Ile Pro Leu Leu His Ser Cys Leu Ser Gln Pro Phe Leu
        930                 935                 940

Arg Phe Arg Ala Cys Ile Val Phe Asp Ser His Asn Glu Thr Tyr Ser
945                 950                 955                 960

Lys Cys Val Phe Arg Phe Lys Gly Ser Phe Gln Asn Cys Ser Asp Ser
                965                 970                 975

Tyr Asn Gln Ala Gln Asp Phe Cys Ala Val Thr Glu Asp Tyr Leu Ile
        980                 985                 990

Tyr Ser Tyr Glu Lys Asp Gly Cys  Leu Phe Val Leu Asp  Tyr Gln Met
        995                 1000                1005

Ser Gln  Ile Pro Leu Glu Met  Asn Phe Asp Gly Leu  Asp Leu Lys
    1010                 1015                1020

Ile His  Ile Val Asp Cys Tyr  Asn Ala Lys Ile Lys  Gly Trp Gly
    1025                 1030                1035

Ile Arg  Ile Leu Glu Glu Asp  Cys Ser Ser Ala Asp  Asn Arg Leu
    1040                 1045                1050

Gly Tyr  Pro Asn Ile Leu Pro  His Val Phe Glu Ala  Asp Glu Cys
    1055                 1060                1065

Asn Met  Arg Leu Val Asn Val  Glu Ala Asn Asp Ala  Val Thr Glu
    1070                 1075                1080

Arg Ser  Gly Met Arg Arg Ser  Lys Ser Thr Ile Leu  Trp Glu Gly
    1085                 1090                1095

Val Val  His Ala Val Pro Leu  Phe Leu Ser Glu Ile  Val Pro Ala
    1100                 1105                1110

Gln Leu  Lys Gly Gly Leu Asn  Ile Val Phe Gln Leu  Met Val Thr
    1115                 1120                1125

Ile Gly  Ile Leu Ile Ala Asn  Leu Val Asn Tyr Phe  Thr Ala Thr
```

| | | | | | | | | | | |
|---|---|---|---|---|---|---|---|---|---|---|
| | | 1130 | | | 1135 | | | 1140 | | |
| Val | His | Pro | Asn | Gly | Ser | Arg | Ile | Ala | Leu | Gly Gly Ala Ala Ile |
| | 1145 | | | | 1150 | | | 1155 | | |
| Pro | Ala | Val | Ile | Leu | Leu | Leu | Gly | Ser | Leu | Ile Ile Cys Glu Thr |
| | 1160 | | | | 1165 | | | 1170 | | |
| Pro | Thr | Ser | Leu | Ile | Glu | Arg | Asn | Lys | Asn | Glu Glu Gly Arg Glu |
| | 1175 | | | | 1180 | | | 1185 | | |
| Thr | Leu | Arg | Lys | Ile | Arg | Gly | | | | |
| | 1190 | | | | 1195 | | | | | |

<210> SEQ ID NO 10
<211> LENGTH: 8102
<212> TYPE: DNA
<213> ORGANISM: Artificial Sequence
<220> FEATURE:
<223> OTHER INFORMATION: nucleotide sequence of the T-DNA 35S::CRT

<400> SEQUENCE: 10

```
aattcaacg gtatatatcc tgccagtact ttgtggcgct ctatcatagc tataaaccta      60
ttcagcacaa tatcgattaa gggccccctc gagggcgatc gctacgtacc tgcaggcccg    120
ggttaattaa gcggccgcaa catggagtca aaaattcaga tcgaggatct aacagaactc    180
gccgtgaaga ctggcgaaca gttcatacag agtcttttac gactcaatga caagaagaaa    240
atcttcgtca acatggtgga gcacgacact ctcgtctact ccaagaatat caagatacag    300
gtctcagaag accaaagggc tattgagact tttcaacaaa gggtaatatc gggaaacctc    360
ctcggattcc attgcccagc tatctgtcac ttcatcaaaa ggacagtaga aaaggaaggt    420
ggcacctaca aatgccatca ttgcgataaa ggaaaggcta tcgttcaaga tgcccctgcc    480
gacagtggtc ccaaagatgg accccacccc acgaggagca tcgtggaaaa agaagacgtt    540
ccaaccacgt cttcaaagca agtggattga tgtgatatct ccactgacgt aagggatgac    600
gcacaatccc actatccttc gcaagaccct tcctctatat aaggaagttc atttcatttg    660
gagaggactc gagctcattt ctctattact tcagccataa caaaagaact ttttctctt    720
cttattaaac caaaaccatg gctctctcat tagcttcttc tccttcctct tgtcgcactt    780
ggttgtacga tgtttttcct agcttcagtg gggtagacgt tcgtgttact ttcctcagcc    840
acttgttgaa ggagtttgac aaaaagttga tcactgcttt caaagacaac agatcgaga    900
gaagtcgatc actggatccc gagcttaaac aagccattaa agattcgagg atcgcagtgg    960
ttatcttctc ccaaaactat gcctcttcaa gctggtgtct taatgagttg ttagagatag   1020
tcaagtgtgg tcaaatggtg atacctgttt tctaccggtt ggatccttcc catgtgagga   1080
aacaaaccgg tgactttggt aagttctttg aagaaacatg caacaacaaa acagaggaag   1140
agaaaataca gtggaggaga gctttgaccg atgtagccaa tactctcggg tatcattcag   1200
taaactggta cggttttatg cttcttttga ataaaggtta gacttctggt tgctaggggg   1260
tgatattatc tttcttattg ttaggggtaa cgaagctgca atgattgaag aaatcgccaa   1320
tgatgttttg gataaactac ttttaacttc atcgaaggat tcagagaact ttgtgggcat   1380
cgaagatcat gttgcaaaac tgagtgtatt gctgcagttg gacgcggagg aagtgaggat   1440
ggttggttta tgggggttcct cagggatcgg caagactaca attgcaagag ttctgttca   1500
acgactttct cgacacttcc gaggtagcat tttcatagac agggctttcg tatctaagac   1560
tatgaaatt ttcaaggcag ctaatccgga cgactataac atgaagctgc atttgcaaag   1620
aaatttccta tctgaaatct taggtaaagg agacataaag ataaatcatt tgagtgcagt   1680
```

```
tggggagagg ctgaagaatc agaaagttct tattttcatt gatgattttg atgatcaagt    1740
tgtgctagaa gccttggttg gtcaaactca atggtttgga agtgggagca gaatcgttgt    1800
ggttacaaat gataagcagt atctaagggc ccatgggatt aatcacattt acaaggtctg    1860
tctcccaact aaaaagctag ctgttgagat gttatgtcga tctgctttca ggaaaaaggc    1920
tgcacctgaa ggttttgagg agcttgtagc taaagttaca ggacttgctg gtagtcttcc    1980
tttaggtctt aatgttttgg gttcatatct acggggaagg acaaggagt actggatgga     2040 tttgttgcca aggcttcaga atggtttaga tgggaaaatt gagaagacat tgagagtcag    2100
ctacgatgga ttaacaagcg aagaagataa agcgttattt cgccatattg catgcctttt    2160
ccagtgggaa aaagtcacat acctgaagtt gctgctcgct gatagtgggt tgagtgttac    2220
ggttgggctg gaaaacctag ctgataagtc cctcattcat gtaagagagg attatgtgaa    2280
gatgcaccgt ttgttagaag agatgggtag acgtattgtt aggcttgacg agcctgaaaa    2340
acgagaattt ctggtggacg cacaagatat ctgtgatgta ctcagtcaag acactgtaag    2400
ttatctctta tgttcgtgct cctttcagtc aataaataag atttagagca tgccatttta    2460
taagcaaaac taatacttga tattatataa ttttcagggt actcataaga tattgggtat    2520
aaaattgaat attgatgaga ttgatgaact gaatgtgcat gagaatgcct tcaaagggat    2580
gcgcaatctg cgtttcctgg aaattcactc acaaaaccgt catgagtttg aaacgaaga    2640 agttagaatt cacttacctg aaaacttcga ctatttgcct cctaaactta aatattgga    2700 ttggtatgaa tatccaatga gatgtctgcc ttctaagttt cgtcctgaaa aactcgtcaa    2760
gctcaaaatg gtgaatagca agctcgagaa gctgtgggaa gggattgtgg taagttttga    2820
gaatagtttg tgatgttatt tgtagtaaga ctaatctta ttttattttt tggatgacaa     2880
tcttgttcta ctgagctcat gtgttctgtt cctttttttt tttgttgagt acagtcgctt    2940
acatgtctta aaaagatgaa tatgtcggga tctcaaaact tgatagaaat gccagatctt    3000
tcaaaggcca ccaatctgga gacactatat cttgaggatt gctttagttt ggtcaagctt    3060
ccttcctcta ttccacaccc caacaaactg acgacattaa tcttgaagaa ctgtcgaaat    3120
gtggagacta ttccaattgg cattagcctc aaatctctta aaaacctacg tactgatggt    3180
tgctcacgga tgaggacttt tccccaaatc tcaagcacca tcgaagatgt ctacataggc    3240
gcaacatcca ttgaagaaat accttcaaat ttgagtttgt gtttcgagaa ctccatacc    3300 tttacgatgc acagcccaaa gaaactatgg gaaagagtgc aggtatgtat gtagttccaa    3360
actttgtgtg tttctccaat ctgttttacg ttatagatat tagataatgg tgcaaatgaa    3420
actaaggtta tattgtattt atcggaggga agaagagtag cgctgaatat gattttgtgt    3480
atttggttca gcttcttact ctcctcacga cgatcatgtc tccctctttg tggtatctgg    3540
atctctcgga taaccctggc ttggtggagc ttccttcttc atttaagaat ctccataacc    3600
tgaggagatt ggaaattaga aactgcgtaa atctggaaac tcttcccacc ggaatcaacc    3660
tcggatctct caaaatccta gatctcaggg gatgctcacg gttgaggact tttcctgata    3720
tctcaaccca catcacacat ctttatctaa gcggaacagg gattgaagag attccttgtt    3780
cgattgagaa attctccagg cttggctccc tacatatgaa cggatgcaac aatttggaat    3840
atgtaaacct aaaccttttt aaactcaaac atcttcacga agtcgacttt tcagactgca    3900
agtgcttaaa cttggatcaa gaagctctgt ttcaaaagaa aacatattca gtttgtcaac    3960
tgaagttgtc aggtgaagaa gtgccttcat atttcacgca ccgtactact ggaacctcct    4020
```

```
cctctctcac cattcctcta cttcacagct gtatctcaca atcattcctc cgattcaggg    4080
cttgtattgt gtttgattcg gacaaggaca atgagtcata tagcagatgt gcctttagat    4140
tcaaaggcag ttttcggaac tgctctgatt cctataatca ggcacaagac ttctgcgcag    4200
tcacggatga ttataagatc cgttcatata agaaggatgg ttgtctgctt gtattagact    4260
accagatgtc tcaaatccct ttagaaatga acttcgatgg cctggatctg aagattcata    4320
ttgattattg tcgttctgct aaaataaaag gatggggtat acgaatctta gaggaggact    4380
gttcatcggc agacaaccga cttggttatc caaacattct accacatgtt tttgaagccg    4440
atgaatgcaa tgaggctggt gaatgtggga ggcaaatgat gtagtgacgg aaagaagcgg    4500
gtaaaggcat taatcatgaa cttatcacag tattttctat atcataattt cttgtactga    4560 gactttttt tcttttctg cagatttcgt gaataaactt ttgattgtgt taggttgtaa    4620
cgcagagcat ctaaaattag gaattaagag agattcccat ccaacttgct tgtggatctt    4680
agtatgcgga gaagtaagag cacaaaattg tgggaaggag tagtgcatgt atgttttctt    4740
caaccttcct tcctttatac tagttcttac aaaaatggtt atgcctggca gatctctaga    4800
aatgacctaa cattattgtg tgtacccttaa attctcaggc agtgcctctt tttctatcag    4860
agattgctcc tgcacagctc aggggaggtc tcaacattgt attccaactc atggtcacaa    4920
ttggaatcct aatagccaac cttgtcaact acttcactgc caccgttcac cctaacggat    4980
ggcgaatcgc cctcggtgga gccgcaatcc ccaccgttat cctagtcttc ggttcactga    5040
tcatctgcga gactcccacg agcttcatag agcgcaagtg ttgaaaacgc gtggcgcgcc    5100
taagctagct atatcatcaa tttatgtatt acacataata tcgcactcag tctttcatct    5160
acggcaatgt accagctgat ataatcagtt attgaaatat ttctgaattt aaacttgcat    5220
caataaattt atgttttgc ttggactata ataccgact tgttatttta tcaataaata    5280
tttaaactat atttctttca agatgaattc gatatcatta ccctgttatc cctaaagctt    5340
attaatataa cttcgtatag catacattat acgaagttat gtttcaaatt tattatgtgt    5400
tttttttccg tggtcgagat tgtgtattat tctttagtta ttacaagact tttagctaaa    5460
atttgaaaga atttactta agaaaatctt aacatctgag ataatttcag caatagatta    5520
tatttttcat tactctagca gtattttgc agatcaatcg caacatatat ggttgttaga    5580
aaaaatgcac tatatatata tatattattt tttcaattaa aagtgcatga tatataatat    5640
atatatatat atatatatgt gtgtgtgtat atggtcaaag aaattcttat acaaatatac    5700
acgaacacat atatttgaca aaatcaaagt attacactaa acaatgagtt ggtgcatggc    5760
caaaacaaat atgtagatta aaaattccag cctccaaaaa aaatccaag tgttgtaaag    5820 cattatatat atatagtaga tcccaaattt ttgtacaatt ccacactgat cgaatttta    5880 aagttgaata tctgacgtag gattttttta atgtcttacc tgaccattta ctaataacat    5940
tcatacgttt tcatttgaaa tatcctctat aattatattg aatttggcac ataataagaa    6000
acctaattgg tgatttattt tactagtaaa tttctggtga tgggctttct actagaaagc    6060
tctcggaaaa tcttggacca aatccatatt ccatgacttc gattgttaac cctattagtt    6120
ttcacaaaca tactatcaat atcattgcaa cggaaaaggt acaagtaaaa cattcaatcc    6180
gatagggaag tgatgtagga ggttgggaag acaggcccag aaagagattt atctgacttg    6240
ttttgtgtat agttttcaat gttcataaag gaagatggag acttgagaag ttttttttgg    6300
actttgttta gctttgttgg gcgtttttt ttttgatca ataactttgt tgggcttatg    6360
atttgtaata ttttcgtgga ctctttagtt tatttagacg tgctaacttt gttgggctta    6420
```

```
tgacttgttg taacatattg taacagatga cttgatgtgc gactaatctt tacacattaa    6480
acatagttct gttttttgaa agttcttatt ttcatttta tttgaatgtt atatatttt     6540 ctatatttat aattctagta aaaggcaaat tttgctttta aatgaaaaaa atatatattc    6600
cacagtttca cctaatctta tgcatttagc agtacaaatt caaaaatttc ccatttttat   6660
tcatgaatca taccattata tattaactaa atccaaggta aaaaaaaggt atgaaagctc    6720
tatagtaagt aaaatataaa ttccccataa ggaaagggcc aagtccacca ggcaagtaaa    6780
atgagcaagc accactccac catcacacaa tttcactcat agataacgat aagattcatg    6840
gaattatctt ccacgtggca ttattccagc ggttcaagcc gataagggtc tcaacacctc    6900
tccttaggcc tttgtggccg ttaccaagta aaattaacct cacacatatc cacactcaaa    6960
atccaacggt gtagatccta gtccacttga atctcatgta tcctagaccc tccgatcact    7020
ccaaagcttg ttctcattgt tgttatcatt atatatagat gaccaaagca ctagaccaaa    7080
cctcagtcac acaaagagta aagaagaaca atggacccag aacgacgccc ggccgacatc    7140
cgccgtgcca ccgaggcgga catgccggcg gtctgcacca tcgtcaacca ctacatcgag    7200
acaagcacgg tcaacttccg taccgagccg caggaaccgc aggagtggac ggacgacctc    7260
gtccgtctgc gggagcgcta tccctggctc gtcgccgagg tggacggcga ggtcgccggc    7320
atcgcctacg cgggcccctg gaaggcacgc aacgcctacg actggacggc cgagtcgacc    7380
gtgtacgtct ccccccgcca ccagcggacg ggactgggct ccacgctcta cacccacctg    7440
ctgaagtccc tggaggcaca gggcttcaag agcgtggtcg ctgtcatcgg gctgcccaac    7500
gacccgagcg tgcgcatgca cgaggcgctc ggatatgccc ccgcggcat gctgcgggcg     7560 gccggcttca gcacgggaa ctggcatgac gtgggttct ggcagctgga cttcagcctg      7620
ccggtaccgc ccgtccggt cctgcccgtc accgagatct gatctcaccc gtctaggatc     7680
ccccgatgag ctaagctagc tatatcatca atttatgtat tacacataat atcgcactca    7740
gtctttcatc tacggcaatg taccagctga tataatcagt tattgaaata tttctgaatt    7800
taaacttgca tcaataaatt tatgtttttg cttggactat aatacctgac ttgttatttt    7860
atcaataaat atttaaacta tatttctttc aagataaaca taacttcgta tagcatacat    7920
tatacgaagt tatcaaaacg tcgtgagaca gtttggttaa ctataacggt cctaaggtag    7980
cgatcgaggc attacggcat tacggcactc gcgagggtcc gaatctatgt cgggtgcgga    8040
gaaagaggta atgaaatggc aattcgagca tggagccatt tacaattgaa tatatcctgc    8100
cg                                                                   8102

<210> SEQ ID NO 11
<211> LENGTH: 121
<212> TYPE: DNA
<213> ORGANISM: Brassica napus

<400> SEQUENCE: 11
atgatctttc atcaaaatat cggatgagaa agcttgaagc ttcgggactg ctcatatact     60
attaagkaaa atagtatttg tgtataaaga agtctattag ttagtaaaca aattgagaga    120
a                                                                    121

<210> SEQ ID NO 12
<211> LENGTH: 121
<212> TYPE: DNA
<213> ORGANISM: Brassica napus
```

```
<400> SEQUENCE: 12
cttctggttt gatacckgtt magmaaatgt catcggtcrg tctgatttga ttgaagaaac        60
gggtaagttg tgcagagact gtgaagctca aggcataggc atagctagca attattcaac      120
c                                                                      121
```

BRASSICA PLANT RESISTANT TO PLASMODIOPHORA BRASSICAE (CLUBROOT)

CROSS-REFERENCE TO RELATED APPLICATIONS

This application is a National Stage Entry of PCT/US2019/022601, filed Mar. 15, 2019, which claims priority to EP application Ser. No. 18/162,162.4, filed Mar. 16, 2018, the disclosures of each of which are hereby incorporated by reference in their entireties.

FIELD OF THE INVENTION

The invention relates to the field of disease control in Brassicacea. Provided are methods for the production of clubroot resistant plants through introduction of a clubroot resistance gene in their genome. Also provided are B. napus plants and seeds comprising one or more clubroot resistance loci in their genome. Further provided are detection tools for detecting the presence of one or more resistance alleles in B. napus plants, tissue or seeds, as well as methods for transferring one or more resistance loci to other Brassica plants and methods for combining different resistance loci in hybrid seeds and plants. Methods for enhancing durability of resistance to Plasmodiophora brassicae are also provided, as well as uses of the plants and seeds and the processes or kits of the invention.

BACKGROUND OF THE INVENTION

Clubroot is a disease caused by Plasmodiophora brassicae which affects the Brassicaceae family of plants, including many important vegetable and broad acre crops. All members of the family Brassicaceae are thought to be potential hosts for Plasmodiophora brassicae (Dixon, 2009, J Plant Growth Regul 28: 194). Susceptible cultivated crops include all varieties of B. oleracea, the Occidental Cole vegetables (Brussels sprout, cabbages, calabrese/green broccoli, cauliflower, culinary and fodder kale, kohlrabi); B. rapa (syn. B. campestris) including turnip, turnip rape, sarson, and the enormous range of Oriental variants which provide leaf and root vegetables such as Brassica rapa var. pekinensis and B. rapa var. chinensis (Chinese cabbages); B. napus including swede (rutabaga), oil seed rape, and fodder rape; and seed, condiment (mustard), and vegetable crops derived from B. carinata, B. nigra, and B. juncea. Related genera such as radish (Raphanus), cruciferous weeds, for example, Sinapis, and decorative ornamentals including stocks (Matthiola spp) and wallflower (Cheiranthus cheiri) can be infected. The scientific model plant Arabidopsis is also susceptible (Dixon, 2009, supra).

Clubroot disease symptom development is characterized by the formation of club-shaped galls on the roots of affected plants. As a result, the nutrient and water uptake by infected roots is inhibited. Above-ground symptoms include wilting, stunting, yellowing and premature senescence (Hwang et al, 2012, Mol Plant Pathol 13: 105).

Clubroot disease is estimated to be present in approximately 10% of all areas where host plants are cultivated (Diederichsen et al, 2009, J Plant Growth Regul 28: 265). Clubroot has been largely a disease of vegetable crops in the last century. However, in 2003, 12 clubroot-infested commercial fields were found in the central part of the province of Alberta. Thereafter, the number of fields with confirmed clubroot infestations has increased steadily, and, by 2010, more than 560 fields (over 35 000 ha) in Alberta had been identified as being infested with P. brassicae (Hwang et al., 2012, supra). Yield losses of 80%-91% were reported in studies with canola grown on clubroot-infested fields in Quebec. Seed quality was also reduced significantly, with declines of 4.7%-6.1% in oil content and 13%-26% in 1000-seed weights (Hwang et al., 2012, supra).

Plant resistance is a powerful tool to combat clubroot disease. Breeding for clubroot resistance focuses today on Chinese cabbage (B. rapa spp. Pekinensis) in Japan and Korea, oilseed rape in Germany and Sweden, and several B. oleracea vegetables. Recently released resistant cultivars belong to three Brassica species: B. napus, B. oleracea, and B. rapa (Diederichsen et al., 2009, supra).

Resistant sources of the European fodder turnips (B. rapa ssp, rapifera) have been identified, which have been used to transfer the clubroot resistance genes to Chinese cabbage. At least three independent dominant genes, which confer differential (race-specific or vertical) resistance to particular pathotypes of P. brassicae, appear to be present in turnip genotypes (Piao et al., 2009, J Plant Growth Regul 28: 252). Eight possible clubroot resistance genes present in B. rapa have been identified through QTL mapping: CRa from resistant source ECD02, CRb from Gelria R, Crr1, Crr2 and Crr4 from Siloga, Crr3 from Milan White, and CRk and CRc from Debra. Crr 1, Crr2, Crr 3, Crr4 and CRc are mapped to chromosomes R8, R1, R3, R6 and R2, respectively. CRa, CRb and CRk with Crr3 are mapped on the same linkage group of R3, but they are not located in the same chromosome region, except for CRk and Crr3 (Piao et al., 2009, supra; Sakamoto et al., 2008, Theor Appl Genet 117:759).

In B. oleracea, completely resistant accessions have been rarely identified. The inheritance of the clubroot resistance in B. oleracea appears polygenic and controlled by many dominant alleles with predominance of additive effects of with incomplete dominance. It has also been suggested that one of the resistances studied is controlled by two complementary genes (Piao et al., 2009, supra). At least 22 QTLs have been found in B. oleracea, indicating a complex genetic basis of clubroot resistance in B. oleracea. As the different mapping studies used different clubroot resistance sources and different P. brassicae isolates, a comparison of these QTLs is not possible (Piao et al., 2009, supra).

Clubroot resistance has also been observed in several B. napus cultivars. At least 22 QTLs for clubroot resistance have been identified in B. napus. A major gene, Pb-Bnl, has been mapped onto linkage group DY4, and at least two additive QTLs have been identified on chromosomes DY4 and DY15, respectively. In addition, epistatic interactions between nine regions with or without additive effects have been located. A major gene and two recessive genes derived from ECD04 have been identified in double-haploid populations. In resynthesized B. napus developed by crossing cv. Bohmerwaldkohl (B. oleracea) and ECD-04 (B. rapa), nineteen QTLs expressing resistance to seven isolates were detected on eight chromosomes, four of which were closely linked to each other on chromosome N03, and three were linked on chromosome N08. Genes CRk and Crr3 are located in the similar region of PbBn-k-2, PbBn-1-1, and PbBn-01: 60-1 on N03. CRa and CRb are independent from them. PbBn-01.07-2, PbBn-1-2, and PbBn-a-1 are linked to BRMS088 on chromosome N08 in B. napus, which is also linked with Crr1 on R8 in B. rapa. PbBn-k-1 is located on chromosome N02. The QTLs located on N03 and N19 contribute strong effects and confer broad-spectrum resistance (Piao et al., 2009, supra; and Werner et al., 2008, Theor Appl Genet 116:363). A clubroot resistant loci has also been recently identified which relates to resistance to various Plasmodiophora brassicae pathotypes including pathotype 5× (WO2016/176358).

The CRa gene of *Brassica rapa* has been fine-mapped and a TIR-NBS-LRR gene has been identified as the CRa gene (Ueno et al., 2012, Plant Mol Biol 80: 621). The Crr1 gene has been mapped and isolated from the *B. rapa* European fodder turnip "Siloga". Crr1a also encodes a TIR-NB-LRR disease resistance protein (Hatakeyama et al., 2013, PLOS one 8: e54745 and WO2012/039445).

The CRb gene from *B. rapa* has been fine-mapped to a 140 kb genomic region. In this region, in which fourteen functional proteins were predicted, amongst which are a Rho family proteins and two TIR-NBS-LRR proteins, which could be candidate genes for CRb (Kato et al., 2013, Breeding Science 63: 116).

To increase the durability of clubroot-resistant cultivars, the combination of the different clubroot resistance genes into a single line will be an important means for breeding cultivars with resistance to a broader spectrum of physiological races. Therefore, in order to stack genes without linkage drag using marker-assisted selection and transgenic approaches, there remains a need to develop molecular markers linked to the clubroot resistance genes. This invention provides the sequence of a clubroot resistance locus from a resistant *Brassica napus* line, as herein after described in the different embodiments, examples and claims.

SUMMARY OF THE INVENTION

In one aspect, the invention provides a protein capable of conferring clubroot resistance comprising an amino acid sequence selected from the group consisting of a) an amino acid sequence of SEQ ID NO: 3 and b) an amino acid sequence having at least 95% sequence identity with the amino acid sequence of SEQ ID NO: 3. An isolated nucleic acid molecule comprising a nucleotide sequence which encodes the protein of the invention is furthermore provided, that is selected from the group consisting of a) a nucleic acid comprising a nucleotide sequence of SEQ ID NO: 1 or SEQ ID 2, b) a nucleic acid sequence having at least 80% identity to the nucleic acid sequence of SEQ ID NO: 1 or SEQ ID NO: 2 and c) a nucleic acid having a complementary sequence to the nucleic acid of a) or b).

It is another object of the present invention to provide a recombinant gene comprising a plant expressible promoter operably linked to a nucleic acid sequence encoding the protein of the invention and optionally, a transcription termination and polyadenylation sequence, preferably a transcription termination and polyadenylation region functional in plants. In another object, said nucleic acid is selected from the group consisting of a) a nucleic acid comprising a nucleotide sequence of SEQ ID NO: 1 or SEQ ID NO: 2; b) a nucleic acid sequence having at least 80% identity to the nucleic acid sequence of SEQ ID NO: 1 or SEQ ID NO: 2; and c) a nucleic acid having a complementary sequence to the nucleic acid of a) or b). In another embodiment, said plant expressible promoter is selected from the group consisting of constitutive promoter, inducible promoter, tissue specific promoter. The plant expressible promoter may be the CaMV35S promoter.

The present invention furthermore provides a plant or plant cells and seeds comprising the recombinant gene according to the invention. The described plant may be a Brassicacae, which may be selected from the group consisting of *Brassica napus, Brassica juncea, Brassica oleracea, Brassica rapa, Brassica nigra* and *Brassica carinata*, and may further comprise at least one other disease resistance gene selected from the group consisting of a clubroot resistance gene, a blackleg resistance gene, a Sclerotinia resistance gene, a Verticillium stripe resistance gene, a Fusarium wilt resistance gene, an Aster Yellows resistance gene, an Alternaria resistance gene, and a Grey Stem resistance gene.

The invention further provides a method for obtaining a clubroot resistant Brassicacae plant, comprising a) introducing or providing the clubroot resistance gene encoding the protein according to the invention to a Brassicacae plant cell, to create a Brassicacae cell, and b) regenerating a plant from said cell. Said Brassicacae plant may be selected from the group consisting of *Brassica napus, Brassica juncea, Brassica oleracea, Brassica rapa, Brassica nigra* and *Brassica carinata*. In another embodiment, the clubroot resistance gene is introduced or provided to the Brassicacae plant cell by providing or introducing to the Brassicacae plant cell the recombinant gene according to the invention. In yet another embodiment, the invention provides another method for obtaining a clubroot resistant Brassicacae plant, comprising a) providing a first *Brassica* plant that comprises the clubroot resistance sequence according to the invention; b) providing a second *Brassica* plant that lacks the clubroot resistance sequence of the invention; c) crossing the first *Brassica* plant with the second *Brassica* plant to provide progeny *Brassica* plant; and d) selecting *Brassica* progeny plant that tests positive for the presence of the clubroot resistance sequence according to the invention as being *Brassica* plant into which the clubroot resistance sequence of the invention has been introduced.

It is another object of the invention to provide a Brassicacae plant obtained by the methods according to the invention. In a further aspect, the Brassicacae plant comprises the clubroot resistance sequence according to the invention and at least one other disease resistance gene, said other disease resistance gene selected from the group consisting of a clubroot resistance gene, a blackleg resistance gene, a Sclerotinia resistance gene, a Verticillium resistance gene, a Fusarium wilt resistance gene, an Aster Yellows resistance gene, an Alternaria resistance gene, and a Grey Stem resistance gene. Such Brassicacae plant may be a *Brassica napus*. Seeds of this Brassicacae plant are also provided and they may be hybrid seeds. With such hybrid seeds, being *Brassica napus* hybrid seeds, and developing into plants, the solid component of the seeds may contain less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid.

Further embodiments disclose a kit for the detection of a CRT clubroot resistance locus in *Brassica* DNA samples, wherein said kit comprises one or more PCR primer pairs, which are able to amplify a DNA marker linked to CRT. The disclosed kit may comprise two primers recognizing CRT and not recognizing the nucleotide sequence of SEQ ID NOs: 4, 5, 7 or 8.

Yet another embodiment provides a method of producing food, feed, or an industrial product comprising obtaining the plant according to the invention or a part thereof, and preparing the food, feed or industrial product from this plant or part thereof. In a further object, said food or feed is oil, meal, grain, starch, flour or protein; or said industrial product is biofuel, fiber, industrial chemicals, a pharmaceutical or a nutraceutical.

BRIEF DESCRIPTION OF THE FIGURES

FIG. 1. Alignment of the nucleotide sequence of the CRT gene (SEQ ID NO: 2) with the CRS genes (SEQ ID NOs: 5 and 8). Nucleotides conserved between CRT and at least one CRS are indicated by an asterisk.

FIG. 2. Alignment of the amino acid sequence of the CRT protein (SEQ ID NO: 3) with the CRS proteins (SEQ ID NOs: 6 and 9). Amino acid residues conserved in all proteins are indicated by an asterisk, conserved amino acid substitutions between CRT and at least one CRS are indicated by a semi colon, amino acids present in one of the CRS but absent from both CRT and the other CRS are indicated with a dash. The TIR domain in SEQ ID NO: 3 is indicated by a grey shadow, the NB-ARC domain is indicated by a box, and the LRR domain is indicated by an underline.

DETAILED DESCRIPTION

Figure 3:
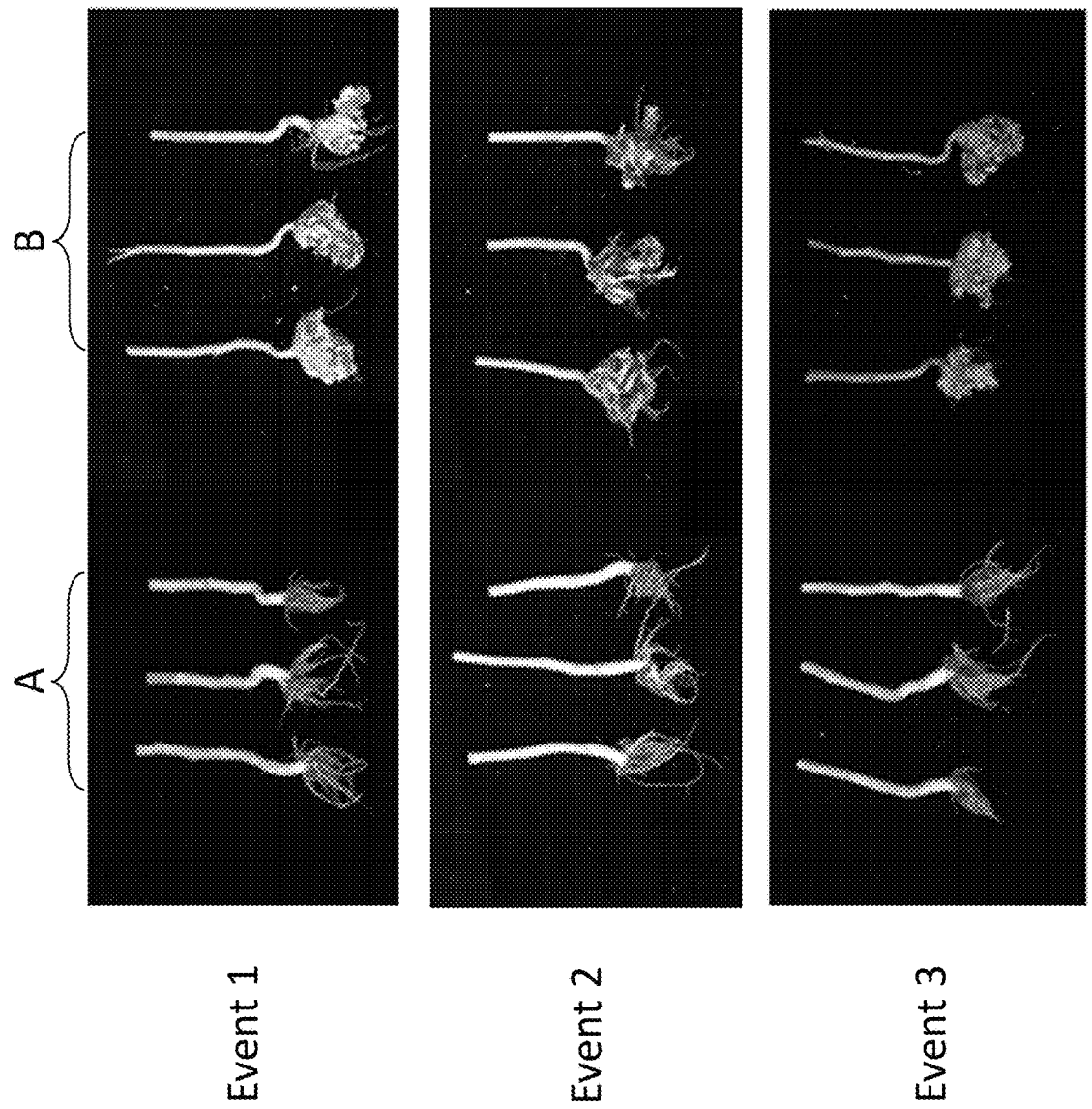
FIG. 3. Result of the clubroot resistance assay performed on three transgenic lines (events) expressing CRT (A) and their respective null segregant (B) at 60 dpi (days post infection).

The current invention is based on the identification of a CRT clubroot resistance gene in *Brassica*.

In one aspect, the invention provides a protein capable of conferring clubroot resistance comprising an amino acid sequence selected from the group consisting of a) an amino acid sequence of SEQ ID NO: 3 and b) an amino acid sequence having at least 95% sequence identity with the amino acid sequence of SEQ ID NO: 3. An isolated nucleic acid molecule comprising a nucleotide sequence which encodes the protein of the invention is furthermore provided, that is selected from the group consisting of a) a nucleic acid comprising a nucleotide sequence of SEQ ID NO: 1 or SEQ ID 2, b) a nucleic acid sequence having at least 80% identity to the nucleic acid sequence of SEQ ID NO: 1 or SEQ ID NO: 2 and c) a nucleic acid having a complementary sequence to the nucleic acid of a) or b).

"Clubroot" as used herein refers to the disease caused by the pathogen Plasmodiophora brassicae.

"Clubroot resistance" as used herein refers to resistance to one or more Plasmodiophora brassicae isolates, such as, but not limited to, resistance to the Plasmodiophora brassicae strain CR11 or CR6 corresponding to pathotype 5× (Yu et al., 2017, Sci Rep 7:4516). Said resistance refers to a reduction in damage caused by clubroot infection compared to damage caused on control plants. Damage can be assessed as, for example, formation of club-shaped galls on the roots, occurrence of wilting, stunting, yellowing, premature senescence etc. In particular, a reduction in damage is manifested in a reduced yield loss when plants are grown under disease pressure in the field, compared to control plants. Such reduction in yield loss can, for example, be due to the fact that the infection, reproduction, spread or survival of the pathogen is reduced or prevented in plants with enhanced resistance. Said resistance may also refer to plants that are completely resistant, i.e., plants on which no disease symptoms are found.

Clubroot resistance can be assessed using a scale from zero to three: zero: no clubbing, one: <25% of root system clubbed; two: 25 to 50% of root system clubbed; three: >50% of root system clubbed (Humpherson-Jones, 1989, Tests Agro Cult 10:36). The Disease Index (ID) can be calculated using the following equation:

[(# plants in class 0*0)+([# plants in class 1*1)+(# plants in class 2*2)+(# plants in class 3*3)]/ total number of plants*3

(Strelkov et al., 2006, Can J Plant Pathol 28:467).

It is understood that environmental conditions, such as location, weather conditions and disease pressure, as well as individual perception of the person assessing disease symptoms, can have an effect on the scoring of clubroot resistance. Hence, variation in these factors in comparative tests should be minimized. Any other resistance ratings known in the art can be applied in accordance with this invention to compare the plants of the invention with control plants.

A "protein capable of conferring clubroot resistance" and the gene encoding the protein capable of conferring clubroot resistance, as used herein, are respectively a protein and a gene that confer resistance to a Plasmodiophora brassicae strain. A CRT resistance gene is present, for example, in *Brassica napus* cvs. *Tosca*. A "CRT clubroot resistance gene", "CRT resistance gene" or "CRT gene" can be sufficient for resistance to Plasmodiophora brassicae strain CR11 or CR6 corresponding to pathotype 5× as described by Yu et al., 2017, Sci. Rep 7:4516. A "CRT clubroot resistance gene" or "CRT gene" can also be required together with another CRT clubroot resistance gene for resistance to Plasmodiophora brassicae strain CR11 or CR6 corresponding to pathotype 5×.

A CRT clubroot resistance gene, or CRT gene can encode a CRT amino acid sequence having at least 95%, or at least 98%, or at least 99%, or 100% sequence identity to SEQ ID NO: 3 and comprising the conserved domains described below. A CRT clubroot resistance gene, or CRT gene, can comprise a nucleotide sequence having at least 80%, or at least 85%, or at least 90%, or at least 92%, or at least 95%, or at least 98%, or at least 99%, or 100% sequence identity to SEQ ID NO: 1 or to SEQ ID NO: 2 and comprise the nucleotide sequences encoding the conserved domains described below.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/ 10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The CRT protein according to the invention comprises a conserved Toll-Interleukin receptor domain (TIR-domain, from amino acid position 15 to amino acid position 149 of SEQ ID NO: 3), NB-ARC domain (from amino acid position 190 to amino acid position 453 on SEQ ID NO: 3; van der Biezen and Jones, 1998, Current Biology, Vol 8, 7:R226-R228), and a LRR domain (leucine rich repeat) with one or more LRR motifs (xxLxLxx) (from amino acid position 612 to amino acid position 867 of SEQ ID NO: 3).

The conserved domains in the CRT protein according to the invention are shown in FIG. 1.

Furthermore, it is clear that variants of CRT proteins, wherein one or more amino acid residues have been deleted, substituted or inserted, can also be used to the same effect in the methods according to the invention, provided that the CRT domains are not affected by the deletion, substitution or insertion of amino-acid. These variant CRT proteins may have about 95% sequence identity to any one of the herein mentioned CRT proteins.

Examples of substitutions are the conservative substitutions, i.e. substitutions of one amino-acid by another having similar physiochemical properties. These substitutions are known not to affect the structure of a protein. Such substitutions are achieved by replacing one aminoacid by another aminoacid belonging to the same group as follows:

Group 1: Cysteine (C);
Group 2: Phenylalanine (F), Tryptophan (W) and Tyrosine (Y);
Group 3: Histidine (H), Lysing K) and Arginine (R);
Group 4: Aspartic acid (D), Glutamic acid (E), Asparagine (N) and Glutamine (Q);
Group 5: Isoleucine (I), Leucine (L), Methionine (M) and Valine (V);
Group 6: Alanine (A), Glycine (G), Proline (P), Serine (S) and Threonine (T).

"Isolated nucleic acid" or "Isolated DNA" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

It is another object of the present invention to provide a recombinant gene comprising a plant expressible promoter operably linked to a nucleic acid sequence encoding the protein of the invention and optionally, a transcription termination and polyadenylation sequence, preferably a transcription termination and polyadenylation region functional in plants. In another object, said nucleic acid is selected from the group consisting of a) a nucleic acid comprising a nucleotide sequence of SEQ ID NO: 1 or SEQ ID NO: 2; b) a nucleic acid sequence having at least 80% identity to the nucleic acid sequence of SEQ ID NO: 1 or SEQ ID NO: 2; and c) a nucleic acid having a complementary sequence to the nucleic acid of a) or b). In another embodiment, said plant expressible promoter is selected from the group consisting of constitutive promoter, inducible promoter, tissue specific promoter. The plant expressible promoter may be the CaMV35S promoter.

As used herein a "recombinant gene" refers to a nucleic acid construct which is not normally found in a plant species. A recombinant nucleic acid construct can be DNA or RNA. "Recombinant DNA construct" and "recombinant gene" are used interchangeably to denote a gene in which the promoter or one or more other regulatory regions of the gene are not associated in nature with part or all of the transcribed DNA region, or a gene which is present in a locus in the plant genome in which it does not occur naturally.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) EMBO 1 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

Suitable promoters for the invention are constitutive plant-expressible promoters. Constitutive plant-expressible promoters are well known in the art, and include the CaMV35S promoter (Harpster et al. (1988) *Mol Gen Genet.* 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the Agrobacterium tumefaciens Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant Mol. Biol. 18:675).

A further promoter suitable for the invention is the endogenous promoter driving expression of the gene encoding an CRT protein.

A "transcription termination and polyadenylation region" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

The present invention furthermore provides a plant or plant cell and a seed comprising the recombinant gene according to the invention. The present invention also provides a plant or plant cell and a seed comprising a heterologous CRT gene encoding the protein of the invention but not comprising at least one of the sequences of SEQ ID NOs: 11 and 12. The described plants may be a Brassicacae, and may further comprise at least one other disease resistance gene selected from the group consisting of a clubroot resistance gene, a blackleg resistance gene, a Sclerotinia resistance gene, a Verticillium resistance gene, a Fusarium wilt resistance gene, an Aster Yellows resistance gene, an Alternaria resistance gene, and a Grey Stem resistance gene.

"Brassicaceae" or "Brassicaceae plant" as used herein refers to plants belonging to the family of Brassicaceae plants, also called Cruciferae or mustard family. Examples of Brassicaceae are, but are not limited to, *Brassica* species, such as *Brassica napus, Brassica oleracea, Brassica rapa, Brassica carinata, Brassica nigra*, and *Brassica juncea; Raphanus* species, such as *Raphanus caudatus, Raphanus raphanistrum*, and *Raphanus sativus; Matthiola* species; *Cheiranthus* species; *Camelina* species, such as *Camelina sativa; Crambe* species, such as *Crambe abyssinica* and *Crambe hispanica; Eruca* species, such as *Eruca vesicaria; Sinapis* species such as *Sinapis alba; Diplotaxis* species; *Lepidium* species; *Nasturtium* species; *Orychophragmus* species; *Armoracia* species, *Eutrema* species; *Lepidium* species; and *Arabidopsis* species.

A "*Brassica* plant" refers to allotetraploid or amphidiploid *Brassica napus* (AACC, 2n=38), *Brassica juncea* (AABB, 2n=36), *Brassica* carinata (BBCC, 2n=34), or to diploid *Brassica rapa* (syn. *B. campestris*) (AA, 2n=20), *Brassica* oleracea (CC, 2n=18) or *Brassica nigra* (BB, 2n=16).

The invention further provides a method for obtaining a clubroot resistant Brassicacae plant, comprising a) introducing or providing the clubroot resistance gene encoding the protein according to the invention to a Brassicacae plant cell, to create a Brassicacae cell, and b) regenerating a plant from said cell. Said Brassicacae plant may be selected from the group consisting of *Brassica napus, Brassica juncea, Brassica oleracea, Brassica rapa, Brassica nigra* and *Brassica carinata*. In another embodiment, the clubroot resistance gene is introduced or provided to the Brassicacae plant cell by providing or introducing to the Brassicacae plant cell the recombinant gene according to the invention. In yet another embodiment, the clubroot resistance gene is introduced or provided to the Brassicacae plant cell by a) providing a first *Brassica* plant that comprises the clubroot resistance sequence according to the invention; b) providing a second *Brassica* plant that lacks the clubroot resistance sequence of the invention; c) crossing the first *Brassica* plant with the second *Brassica* plant to provide progeny *Brassica* plant; and d) selecting *Brassica* progeny plant that tests positive for the presence of the clubroot resistance sequence according to the invention as being *Brassica* plant into which the clubroot resistance sequence of the invention has been introduced.

A transgene can be provided to a plant or plant cell using methods well-known in the art. Methods for introduction of genes into plant cells to create transgenic plants are not deemed critical for the current invention and any method to provide plant cells with a transgene suitable for a particular plant species can be used. Such methods are well known in the art and include Agrobacterium-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. Said transgene may be stably integrated into the genome of said plant cell, resulting in a transformed plant cell. The transformed plant cells obtained in this way may then be regenerated into mature fertile transformed plants.

A "molecular marker", or a "marker", as used herein, refers to a polymorphic locus, i.e. a polymorphic nucleotide (a so-called single nucleotide polymorphism or SNP) or a polymorphic DNA sequence (which can be insertion or deletion of a specific DNA sequence at a specific locus, or polymorphic DNA sequences). A marker refers to a measurable, genetic characteristic with a fixed position in the genome, which is normally inherited in a Mendelian fashion, and which can be used for mapping of a trait of interest. Thus, a molecular marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) NAR 23:4407-4414], SSRs or microsatellites [Tautz et al. (1989), NAR 17:6463-6471]. Appropriate primers or probes are dictated by the mapping method used.

The term "AFLP®" (AFLP® is a registered trademark of KeyGene N. V., Wageningen, The Netherlands), "AFLP analysis" and "AFLP marker" is used according to standard terminology [Vos et al. (1995), *NAR* 23:4407-4414; EP0534858; http://www.keygene.com/keygene/techs-apps/]. Briefly, AFLP analysis is a DNA fingerprinting technique which detects multiple DNA restriction fragments by means of PCR amplification. The AFLP technology usually comprises the following steps: (i) the restriction of the DNA with two restriction enzymes, preferably a hexa-cutter and a tetra-cutter, such as EcoRI, PstI and MseI; (ii) the ligation of double-stranded adapters to the ends of the restriction fragments, such as EcoRI, PstI and MseI adaptors; (iii) the amplification of a subset of the restriction fragments using two primers complementary to the adapter and restriction site sequences, and extended at their 3' ends by one to three "selective" nucleotides, i.e., the selective amplification is achieved by the use of primers that extend into the restriction fragments, amplifying only those fragments in which the primer extensions match the nucleotides flanking the restriction sites. AFLP primers thus have a specific sequence and each AFLP primer has a specific code (the primer codes and their sequences can be found at the Keygene website: http://www.keygene.com/keygene/pdf/PRIMERCO.pdf; herein incorporated by reference); (iv) gel electrophoresis of the amplified restriction fragments on denaturing slab gels or cappilaries; (v) the visualization of the DNA fingerprints by means of autoradiography, phosphor-imaging, or other methods. Using this method, sets of restriction fragments may be visualized by PCR without knowledge of nucleotide sequence. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment. It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome.

The term "SSR" refers to Simple Sequence Repeats or microsatellite [Tautz et al. (1989), NAR 17:6463-6471]. Short Simple Sequence stretches occur as highly repetitive elements in all eukaryotic genomes. Simple sequence loci usually show extensive length polymorphisms. These simple sequence length polymorphisms (SSLP) can be detected by polymerase chain reaction (PCR) analysis and be used for identity testing, population studies, linkage analysis and genome mapping.

It is understood that molecular markers can be converted into other types of molecular markers. When referring to a specific molecular marker in the present invention, it is understood that the definition encompasses other types of molecular markers used to detect the genetic variation originally identified by the specific molecular markers. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [(2001), *Mol Gen Genomics* 265(2):207-214], Negi et al. [(2000), *TAG* 101: 146-152], Barret et al. (1989), *TAG* 97:828-833], Xu et al. [(2001), *Genome* 44(1):63-70], Dussel et al. [(2002), *TAG* 105:1190-1195] or Guo et al. [(2003), *TAG* 103:1011-1017]. For example, Dussel et al. [(2002), *TAG* 105:1190-1195] converted AFLP markers linked to resistance into PCR-based sequence tagged site markers such as indel (insertion/deletion) markers and CAPS (cleaved amplified polymorphic sequence) markers.

Suitable molecular markers are, for example SNP markers (Single Nucleotide Polymorphisms), AFLP markers, microsatellites, minisatellites, Random Amplified Polymorphic DNA's (RAPD) markers, RFLP markers, Sequence Characterized Amplified Regions (SCAR) markers, and others, such as TRAP markers described by Hu et al. 2007, Genet Resour Crop Evol 54: 1667-1674).

Methods and assays for marker detection, or for analyzing the genomic DNA for the presence of a marker, are widely known in the art. The presence of a marker can, for example be detected in hybridization-based methods (e.g. allele-specific hybridization), using Taqman, PCR-based methods, oligonucleotide ligation based methods, or sequencing-based methods.

A useful assay for detection of SNP markers is for example KBioscience Competitive Allele—Specific PCR . For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p1097-1098 for KASP assay method (incorporated herein by reference).

A "molecular marker linked to the CRT clubroot resistance gene", or a "molecular marker linked to the presence of the CRT clubroot resistance gene" as used herein refers to a molecular marker in a region in the genome that inherits with the CRT clubroot resistance gene as a single genetic unit in at least 50% of the cases. Thus, in this respect, the term linked can be a separation of about 50 cM, or less such as about 40 cM, about 30 cM, about 20 cM, about 10 cM, about 7.5 cM, about 6 cM, about 5 cM, about 4 cM, about 3 cM, about 2.5 cM, about 2 cM, or even less. Said "molecular marker linked to the CRT clubroot resistance gene" is thus a marker which is linked to the CRT clubroot resistance gene. Said marker can be based on the CRT clubroot resistance gene itself, such as presence or absence of the CRT clubroot resistance gene.

Suitable are markers that are linked to the CRT clubroot resistance gene can be developed using methods known in the art. New markers suitable for the invention can be developed based on the CRT sequence. It is understood that such markers can be developed by comparing the sequence of the CRT clubroot resistance gene from the resistant Brassicaceae line with the sequence of the same gene in a susceptible Brassicaceae line; identifying a specific sequence region in the CRT clubroot resistance gene which does not occur in the corresponding gene of the susceptible Brassicaceae line. A molecular marker linked to the CRT clubroot resistance gene can thus be a marker detecting the presence of the CRT clubroot resistance gene, or can be a marker directly detecting the presence of the sequence of SEQ ID NOs: 1 or 2. A molecular marker linked to the CRT clubroot resistance gene can also be a marker in the sequences flanking the CRT clubroot resistance gene, which is polymorphic between lines comprising the CRT clubroot resistance gene and lines lacking, but which inherits with the CRT clubroot resistance gene as a single genetic unit in at least 50% of the cases.

The absence of the CRT clubroot resistance gene can be determined by the absence of marker alleles that are linked to the presence of the CRT clubroot resistance gene (CRT clubroot resistance marker alleles. Furthermore, markers suitable to determine the absence of the CRT clubroot resistance gene can be marker alleles which are linked to the CRS clubroot susceptibility gene.

Analysis for the presence of markers according to the invention can be performed with a first primer and a second primer, and, optionally, a probe, selected from the group consisting of a first primer consisting of a sequence of 15 to 30 nucleotides, or 15 to 25 nucleotides, or 18 to 22 nucleotides of the CRT clubroot resistance genes according to the invention, a second primer being complementary to a sequence of 15 to 30 nucleotides, or 15 to 25 nucleotides, or 18 to 22 nucleotides of the CRT clubroot resistance genes according to the invention, and wherein the distance between said first and said second primer on the CRT clubroot resistance gene is between 1 and 400 bases, or between 1 and 150 bases, and wherein the first primer is located, with respect to the CRT coding sequence, upstream of said second primer, and a probe which is identical to at least 15 nucleotides, or at least 18 nucleotides, but not more than 25 nucleotides, or not more than 22 nucleotides of the sequence of the CRT clubroot resistance gene between said first and said second primer, provided that either the sequence of the first primer, or the sequence of the second primer, or the sequence of said probe is not present in the corresponding locus in a susceptible Brassicaceae plant. Said probe may be labelled, such as, for example, described in U.S. Pat. No. 5,538,848.

Analysis for the presence of markers according to the invention can be performed with a first and second primer as described above recognizing both the CRT sequence and the corresponding gene in the susceptible Brassicaceae line, a first probe recognizing a sequence of the CRT clubroot resistance gene as described above, but not recognizing a sequence between said first and said second primer in the susceptible Brassicaceaea line, and a second probe recognizing a sequence between said first and said second primer in the susceptible Brassicaceaea line, but not of the CRT clubroot resistance gene, and wherein said the label of the first probe is different from that of the second probe.

Further suitable primers for analysis of the presence of markers according to the invention are markers a first primer as described above recognizing both the CRT sequence and the corresponding gene in the susceptible Brassicaceae line, a second primer recognizing the CRT sequence but not the corresponding gene in the susceptible Brassicaceae line, and a third primer recognizing the corresponding locus in the susceptible Brassicaceae line but not the CRT sequence. Said second and third primer may be labelled as indicated above, and said second primer may contain a label which is different from said third primer.

Identification of PCR products specific for the CRT clubroot resistance genes and for the corresponding gene in the susceptible Brassicaceae line can occur e.g. by size estimation after gel or capillary electrophoresis (e.g. for the CRT clubroot resistance gene and for the corresponding gene in the susceptible Brassicaceae line comprising a number of inserted or deleted nucleotides which results in a size difference between the fragments amplified from the CRT clubroot resistance gene and for the corresponding gene in the susceptible Brassicaceae, such that said fragments can be visibly separated on a gel); by evaluating the presence or absence of the two different fragments after gel or capillary electrophoresis, whereby the diagnostic PCR amplification of the CRT clubroot resistance gene can, optionally, be performed separately from the diagnostic PCR amplification of the corresponding gene in the susceptible line; by direct sequencing of the amplified fragments; or by fluorescence-based detection methods.

"Introducing" or "providing" in connection with the present application may relate to the placing of genetic information in a plant cell or plant by artificial means. This can be effected by any method known in the art for introducing RNA or DNA into plant cells, tissues, protoplasts or whole plants.

It is another object of the invention to provide a Brassicacae plant obtained by the method according to the invention. In a further aspect, the Brassicacae plant comprises the clubroot resistance sequence according to the invention and at least one other disease resistance gene, said other disease resistance gene selected from the group consisting of a clubroot resistance gene, a blackleg resistance gene, a Sclerotinia resistance gene, a Verticillium resistance gene, a Fusarium wilt resistance gene, an Aster Yellows resistance gene, an Alternaria resistance gene, and a Grey Stem resistance gene. Such Brassicacae plant may be a *Brassica napus*. Seeds of this Brassicacae plant are also provided and they may be hybrid seeds. With such hybrid seeds, being *Brassica napus* hybrid seeds, and developing into plants, the solid component of the seeds may contain less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid.

Said clubroot resistance gene may be a Crr2, Crr4, Crr3, CRk, CRc, CR2a, CR2b, pb-3, pb-4, Pb-Bo 1, Pb-Bo2, Pb-Bo3, Pb-Bo4, Pb-Bo5a, Pb-Bo5b, Pb-Bo8, Pb-Bo9a, Pb-Bo9b, Pb-Bn1PbBn-01:60-1, PbBn-01:60-2, PbBn-01: 60-3, PbBn-01:60-4, PbBn-01:07-1, PbBn-01:07-2, PbBn-01:07-3, PbBn-e4x04-1, PbBn-a-1, PbBn-1-1, PbBn-1-2, PbBn-k-1, PbBn-k-2. PbBn-k-3, PbBn-Korp-1, PbBn-Korp-2, PbBn-Korp-3, PbBn-Korp-4, PbBn-Korp-5 as described by Piao et al., 2009, supra, or may be a CRa gene as described by Ueno et al., 2012, supra, a Crr1 gene as described by Hatakeyama et al., 2013, supra and in WO2012/039445, or a CRb gene as described by Kato et al., 2013, supra, a CRL gene as described in WO2017/102923.

Said Blackleg resistance gene may, for example, be BLMR1 and BLMR2 (WO 2011/044694), LepR3 (Larkan et al., 2013, New Phytol 197:595 and WO 2008/101343), or Lem-08-syl (EP 1547462 and US 2005/0142122). Said Sclerotinia resistance gene may be a sclerotinia resistance gene as described in WO 2005/090578.

Said other disease resistance gene may be present in their native chromosomal position. For example, said other disease resistance genes can be introduced by introgression in the plant according to the invention from the cultivar or -species from which they are derived.

A plant which is clubroot resistant refers to a plant assessed at scale zero or one upon natural infection with the clubroot pathogen, or to a plant assessed at scale zero, one or two upon natural infection with the clubroot pathogen. A clubroot resistant population is a population with a disease index (ID) of less than 30%. A plant with increased clubroot resistance is a plant in which the percentage of the root system which is clubbed is decreased with at least 5%, or at least 10%, or at least 15%, or at least 20%, or at least 30%, or at least 40%, or at least 50%, or at least 70%, or at least 95%, or with 100%, i.e. no clubbing, or refers to a population of plants in which the disease index is reduced with at least 3%, or at least 5%, or at least 8%, or at least 10%, or at least 15%, or at least 20%, or at least 30%, or at least 40%, or at least 50%, or at least 70%, or at least 95%, or with 100%, i.e. all plants of the population are classified in class 0 (no clubbing).

Hybrid seeds of the plants according to the invention may be generated by crossing two inbred parental lines, wherein at least one of the inbred parental lines comprises the CRT clubroot resistance genes according to the invention. In order to produce pure hybrid seeds one of the parental lines is male sterile and is pollinated with pollen of the other line. By growing parental lines in rows and only harvesting the F1 seed of the male sterile parent, pure hybrid seeds are produced. To generate male sterile parental lines, the system as described in EP 0,344,029 or U.S. Pat. No. 6,509,516 may be used, wherein a gene encoding a phytotoxic protein (barnase) is expressed under the control of a tapetum specific promoter, such as TA29, ensuring selective destruction of tapetum cells. Transformation of plants with the chimeric gene pTA29:barnase results in plants in which pollen formation is completely prevented [Mariani et al. (1990), *Nature* 347: 737-741]. Cytochemical and histochemical analysis of anther development of *Brassica napus* plants comprising the chimeric pTA29-barnase gene is described by De Block and De Brouwer [(1993), *Planta* 189:218-225]. To restore fertility in the progeny of a male-sterile plant the male-sterile plant (MS parent) is crossed with a transgenic plant (RF parent) carrying a fertility-restorer gene, which when expressed is capable of inhibiting or preventing the activity of the male-sterility gene [U.S. Pat. Nos. 5,689,041; 5,792,929; De Block and De Brouwer, supra]. The use of co-regulating genes in the production of male-sterile plants to increase the frequency of transformants having good agronomical performance is described in WO96/26283. Typically, when the sterility DNA encodes a barnase, the co-regulating DNA will encode a barstar, preferably an optimized barstar gene is used as described in published PCT patent application WO 98/10081. It is understood that different promoters may be used to drive barnase expression in order to render the plant male sterile. Likewise, barstar may be operably linked to different promoters, such as 35S from Cauliflower mosaic virus.

Male sterile plants can also be generated using other techniques, such as cytoplasmic male sterility/restorer systems [e.g. the Ogura system, published US patent application 20020032916, U.S. Pat. No. 6,229,072, WO97/02737, U.S. Pat. No. 5,789,566 or the Polima system of U.S. Pat. No. 6,365,798, WO98/54340 or the Kosena system of WO95/09910, U.S. Pat. No. 5,644,066].

Either the MS parent or the RF parent, or both, may comprise the CRT clubroot resistance genes according to the invention. This can be accomplished by either introducing the CRT clubroot resistance genes into an elite *B. napus* line and then transforming this line with pTA29-barnase or with pNOS-barstar using known methods. Alternatively the CRT clubroot resistance genes can be introduced directly into a transgenic MS or RF parent line, by crossing a plant comprising the CRT clubroot resistance genes with the MS parent or RF-parent, or by transformation of the MS parent or the RF parent. The F1 hybrid seeds generated from the cross between the MS and RF parent will then contain the CRT clubroot resistance genes.

Further embodiments disclose a kit for the detection of a CRT clubroot resistance locus in *Brassica* DNA samples, wherein said kit comprises one or more PCR primer pairs, which are able to amplify a DNA marker linked to CRT. The disclosed kit may comprise two primers recognizing CRT and not recognizing the nucleotide sequence of SEQ ID NOs: 4, 5, 7 or 8.

A "kit", as used herein, refers to a set of reagents for the purpose of performing the method of the invention, more particularly, the identification of the CRT clubroot resistance genes in biological samples or the determination of the zygosity status of plant material comprising the CRT clubroot resistance genes. More particularly, a preferred embodiment of the kit of the invention comprises at least two specific primers for identification of the CRT clubroot resistance genes, or at least two or three specific primers for the determination of the zygosity status. Optionally, the kit can further comprise any other reagent. Alternatively, according to another embodiment of this invention, the kit can comprise at least one specific probe, which specifically hybridizes with nucleic acid of biological samples to identify the presence of the CRT clubroot resistance genes therein, or at least two or three specific probes for the determination of the zygosity status. Optionally, the kit can further comprise any other reagent (such as but not limited to hybridizing buffer, label) for identification of the CRT clubroot resistance genes in biological samples, using the specific probe.

The kit of the invention can be used, and its components can be specifically adjusted, for purposes of quality control (e.g., purity of seed lots), detection of the presence or absence of the CRT clubroot resistance gene in plant material or material comprising or derived from plant material, such as but not limited to food or feed products. The zygosity status of the CRT clubroot resistance gene can be determined by using alternative sets of primers and/or probes that specifically the CRT gene and the corresponding gene in a susceptible *Brassicaceae* line.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a specific nucleic acid sequence under the conditions set forth in the method (such as the conditions of the PCR identification protocol), whereby the specificity is determined by the presence of positive and negative controls. It is standard in the art to design primers recognizing specifically the nucleotide sequence of a given allele of a gene.

Yet another embodiment provides a method of producing food, feed, or an industrial product comprising obtaining the plant according to the invention or a part thereof, and preparing the food, feed or industrial product from this plant or part thereof. In a further object, said food or feed is oil, meal, grain, starch, flour or protein; or said industrial product is biofuel, fiber, industrial chemicals, a pharmaceutical or a nutraceutical.

Further provided is the use of the nucleotide sequence of SEQ ID NOs: 1 or 2 or of the amino acid sequence of SEQ ID NO: 3 to identify homologous clubroot resistance genes.

Homologous clubroot resistance genes can be identified using methods known in the art. Homologous nucleotide sequence may be identified and isolated by hybridization under stringent conditions using as probes a nucleic acid comprising the nucleotide sequence of SEQ ID NOs: 1 or 2 or part thereof. Other sequences encoding CRT may also be obtained by DNA amplification using oligonucleotides specific for genes encoding CRT as primers, such as but not limited to oligonucleotides comprising or consisting of about 20 to about 50 consecutive nucleotides from SEQ SEQ ID NOs: 1 or 2 or its complement. Homologous clubroot resistance genes can be identified in silico using Basic Local Alignment Search Tool (BLAST) homology search with other nucleotide or amino acid sequences. Functionality of the identified homologous clubroot resistance genes can be validated using the methods described herein, such as transforming a the clubroot resistance gene under control of a plant-expressible promoter in a plant not being clubroot resistant.

Hybridization occurs when the two nucleic acid molecules anneal to one another under appropriate conditions. Nucleic acid hybridization is a technique well known to those of skill in the art of DNA manipulation. The hybridization property of a given pair of nucleic acids is an indication of their similarity or identity. Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence. "Stringent hybridization conditions" and "stringent hybridization wash conditions" in the context of nucleic acid hybridization experiments such as Southern and Northern hybridization are sequence dependent, and are different under different environmental parameters. An example of highly stringent wash conditions is 0.15 M NaCl at 72° C. for about 15 minutes. An example of stringent wash conditions is a 0.2× SSC wash at 65° C. for 15 minutes. Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4 to 6× SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code. Very stringent conditions are selected to be equal to the Tm for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1× SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2× SSC, 0.1% SDS at 50° C., more desirably in 7% sodium dodecyl sulfate (SDS), 0.5 M NaPO$_4$, 1 mM EDTA at 50° C. with washing in 1× SSC, 0.1% SDS at 50° C., more desirably still in 7% sodium dodecyl sulfate (SDS), 0.5 M NaPO$_4$, 1 mM EDTA at 50° C. with washing in 0.5× SSC, 0.1% SDS at 50° C., even more desirably still in 7% sodium dodecyl sulfate (SDS), 0.5 M NaPO$_4$, 1 mM EDTA at 50° C. with washing in 0.1× SSC, 0.1% SDS at 50° C.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists: Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, Bacillus firmus, Bacillus firmus strain I-1582, Bacillus subtilis, Bacillus subtilis strain GB03, Bacillus subtilis strain QST 713, Bacillus pumulis, Bacillus. pumulis strain GB34. Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl) sulfinyl]phenyl}-3-(trifluoromethyl)-1H-1,2,4-triazol-5-amine, (1E)-N-[(6-chloropyridin-3-yl)methyl]-N-cyano-N-(2,2-difluoroethypethanimidamide, Bacillus firmus, Bacillus firmus strain 1-1582, Bacillus subtilis, Bacillus subtilis strain GB03, Bacillus subtilis strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention, i.e. a plant cell comprising a CRT clubroot resistance gene as well as plant cells generated according to the methods of the invention, may be non-propagating cells.

The obtained plants according to the invention can be used in a conventional breeding scheme to produce more plants with the same characteristics or to introduce the characteristic of the presence of the CRT gene according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

The sequence listing contained in the file named, BCS18-2008_ST25.txt", which is 74 kilobytes (size as measured in Microsoft Windows®), contains 12 sequences SEQ ID NO: 1 through SEQ ID NO: 12 is filed herewith by electronic submission and is incorporated by reference herein.

In the description and examples, reference is made to the following sequences:
SEQUENCES
SEQ ID No. 1: nucleotide sequence of CRT coding sequence.
SEQ ID No. 2: nucleotide sequence of CRT genomic sequence.
SEQ ID No. 3: amino acid sequence of the CRT protein.
SEQ ID No. 4: nucleotide sequence of CRS1 coding sequence.
SEQ ID No. 5: nucleotide sequence of CRS1 genomic sequence.
SEQ ID No. 6: amino acid sequence of the CRS1 protein.
SEQ ID No. 7: nucleotide sequence of CRS2 coding sequence.
SEQ ID No. 8: nucleotide sequence of CRS2 genomic sequence.
SEQ ID No. 9: amino acid sequence of the CRS2 protein.
SEQ ID No. 10: nucleotide sequence of the T-DNA 35S::CRT.
SEQ ID No. 11: SNP marker locus associated with the clubroot resistance in the Tosca variety.
SEQ ID No. 12: second SNP marker locus associated with the clubroot resistance in the Tosca variety.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, N.Y., in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany. Standard procedures for AFLP analysis are described in Vos et al. (1995, NAR 23:4407-4414) and in published EP patent application EP 534858.

Example 1

Rough Mapping of Clubroot Resistance

Generation of a *Brassica napus* Mapping Population
A Double Haploid (DH) population was made from the F1 cross between a clubroot resistant female DH parent and a clubroot susceptible male DH parent. The population consisted of 199 individuals.
Infinium Genotyping (iSCAN) Analysis of the DH Lines
DNA was extracted from the 199 DH plants and from the 2 parents of the cross using the automated KingFisher DNA extraction method (Thermo Scientific) using the manufacturer's purification kits and protocol.

A custom ~5K (4921) SNP array, an Illumina Infinium II HD BeadChip was designed by screening Bayer propitiatory SNPs, their individual variant loci including their left and right flanking sequences via the Illumina Assay Design Tool (ADT) then selecting most successful custom genotyping assays as described by Ganal et al. (PLOS. Dec. 8, 2011) and Clark, et al. (2016, Theor Appl Genet.129(10): 1887-1899).

Assays were performed as described by the manufacturer's protocol and as described in by Ganal et al. (2011) and Clark, et al. (2016).

Starting with a total of 200 ng (50 ng/µl) of genomic DNA, this is amplified via modified whole genome amplification and enzymically fragmented. The fragmented DNA is hybridized to a single SNP array of a 24 array chip. The position of each oligonucleotide tagged bead is provided in the BeadChip manifest file (*.dmap). In this manner the fragmented DNA sample can hybridise specifically to each bead oligonucleotide which is known to corresponding to a single SNP. Detection of the precise SNP allele is performed by a single base extension, with A/T extension bases being tagged with dinitrophenyl (DNP) and C/G based tagged with biotin. Anti-biotin or anti-DNP antibodies with bound flurophores are lazer exited to emit light signals detected as red and green (respectively) and captured by the Illumina iScan in a high resolution BeadChip image. After images are scanned they are analysed on the Illumina iSCAN system (array reader) where signals are registered according to the corresponding bead map (*.dmap) file and two-colour signal intensity values are extracted for every bead on the image (*.idat). By default, the ICS AutoConvert was enabled, normalising the intensity data and generating genotype calls.

Analysis of BeadArray idat files was performed using GenomeStudioTM Data Analysis Software (GenomeStudio Software V2011.1 (Illumina)). Primary data analyses, such as raw data normalization, clustering, and genotype calling are performed using integrated algorithms (GenTrain & GenCall) in the GenoTyping (GT) Module. Genotype calls are made from BeadChip marker two-colour signal intensities by comparison to canonical genotype clusters. Cluster position identification is performed by the GenTrain algorithm. With one sample precluded due to failed DNA extraction no further poorly performing samples were identified so further sample removal and reclustering of all SNPs was not required. Never-the-less the position of SNP clusters required editing by visualising the Cy3 and Cy5 fluorescence intensity clustering in 2D Cartesian plots and re-centring the clusters. The refined genotype calls were scrutinised further before exporting genotype calls knowing that the parents and the lines of this population were doubled haploids and so any SNPs that failed to show only two-group clustering were not credible: SNPs with more than two call clustered were set to 'no-call'.

Phenotyping of DH Lines

The University of Alberta, AB Canada, collected isolates across western Canada. Some of the isolates were single-spored and characterized as pathotypes 3, 5, 6 and 8 (Strelkov et. al. 2006, Xue et. 2008) based on the differential system of Williams, 1966. Pathotypes 3, 5, 6 and 8 were obtained from the University and each pathotype was individually inoculated onto each DH line separately and phenotyped using a 0-3 scale.

Genetic Mapping

A total of 1608 polymorphic SNP marker instances were observed over the individuals of the DH mapping population (3070 markers were monomorphic, and 243 had more than 10% no-calls). Genetic linkage mapping was performed using MSTMap software (Wu, PLOS. Oct. 10, 2008). Default MSTMap parameters were applied according to online user instructions (http://138.23.178.42/mstmap/). MSTMap finds the optimal molecular marker order and the recombinational distance by computing a minimal spanning tree of the graph associated with the genotyping data. Setting the minimum distance between two markers, via the parameter 'no_map_dist', defined marker dense linkage groups.

Quantitative Trait Locus mapping was performed using R/qtl as described in the "Guide to QTL Map with R/qtl". Briefly, the genetic map was inspected by re-calculating the pairwise recombination fractions (recombination frequencies) and the 'check marker order' process identified problem marker orders than were then corrected using the switch.order' function. With the correct orders, final mapping distances were calculated using the Kosambi mapping algorithm. As the phenotypes were not normally distributed we used a rank-based method (an extension of the Kruskal-Wallis test) for 'Nonparametic interval mapping'

Linked marker genotype groupings were identified by examining the Lod-grouping tree results that ranged from Lod3 to Lod6. With groups of linked markers identified, ordering of the markers was performed using the default calculation options, with the 3rd round option and using the Kosambi mapping function. This analysis led to the identification of a genomic region on chromosome N03 comprising five candidate disease resistance genes.

Example 2

Fine Mapping of Clubroot Resistance and Identification of the CRT Gene

An F2 population of 3000 individuals was made from the F1 cross between a clubroot resistant female parent and a clubroot susceptible male parent. These 3000 F2 were genotyped together with the parents using 99 SNP markers located in the identified genomic interval on N03. This analysis led to the identification of a smaller genomic interval within the identified region on chromosome N03, now comprising only one candidate disease resistance gene, namely the CRT clubroot resistance gene.

The identified CRT gene is a NBS-encoding gene. The genomic sequence of the clubroot resistant allele is provided in SEQ ID NO: 2 while the genomic sequence of two susceptible alleles is provided in SEQ ID Nos: 5 and 8. The corresponding coding DNA sequences are provided respectively in SEQ ID NOs: 1, 4 and 7.

FIG. 1 shows the alignment of the coding sequences of the resistant and susceptible alleles while the alignment of the amino acid sequences of the corresponding resistant and susceptible proteins are given in FIG. 2. Overall, the amino acid sequence of CRT shares at least 90% similarity with the corresponding clubroot sensitive proteins.

Example 3

Validation of the Clubroot Resistance Gene CRT

Construction of a Recombinant Gene Encoding CRT for Constitutive Expression in *Brassica* Cells A DNA molecule having the nucleic acid sequence according to SEQ ID NO: 1 was obtained by PCR cloning.

Using standard recombinant DNA techniques, the constitutive promoter region CaMV35S according to the sequence from nucleotide position 141 to 668 of SEQ ID NO: 10, the 5'UTR sequence including the leader sequence of the chlorophyll a/b binding protein gene of Petunia hybrid according to the sequence from nucleotide position 672 to 731 of SEQ ID NO: 10, the DNA fragment coding for CRT according to the sequence SEQ ID NO: 1 or to the sequence from nucleotide position 738 to 5084 of SEQ ID NO: 10, and the 3' untranslated sequence of the g7 gene of *Agrobacterium tumefaciens* according to the sequence from nucleotide position 5101 to 5304 of SEQ ID NO: 10 were assembled in a vector which contains the bar selectable marker cassette (position 5385 to 7895 of SEQ ID NO: 10) to result in the T-DNA P35S::CRT (SEQ ID NO: 10).

Generation of Transgenic *Brassica* Plants Expressing CRT

The T-DNA vector was introduced into *Agrobacterium tumefaciens* strains containing a helper Ti-plasmid and used to stably transform an in house developed *Brassica napus* line which is susceptible to the clubroot strains CR11 and CR6. Homozygous plants and their respective null segregants were further analyzed as described below.

Clubroot Resistance Assessment of Transgenic *Brassica* Plants Expressing CRT Constitutively and their Respective Null Segregating Line Of all the transgenic lines, or events, produced, 8 were selected based on their effective expression of the CRT transgene in the homozygotes to be phenotyped for Clubroot disease resistance by inoculation with isolate CR6.

The clubroot resistance assessment provided the consistent result that for each lines transformed with and expressing CRT, the homozygous plants are resistant to the disease while the null segregants are susceptible to it. FIG. 3 shows the phenotype observed for 3 of those lines. The homozygous plants develop healthy root systems in spite of the inoculation with the pathogen while the roots of the null segregants develop galls typical of the infection with the clubroot pathogen.

The invention claimed is:

1. A method for obtaining a clubroot resistant *Brassica napus* plant, comprising:
   a) introducing or providing the clubroot resistance gene encoding a protein comprising an amino acid sequence of SEQ ID NO: 3, or an amino acid sequence having at least 95% sequence identity with the amino acid sequence of SEQ ID NO: 3, to a *Brassica napus* plant cell, to create a *Brassica napus* cell, and
   b) regenerating a plant from said cell.

2. A method for obtaining a clubroot resistant *Brassica napus* plant, comprising:
   crossing a first *Brassica napus* plant that comprises a nucleic acid molecule comprising a nucleotide sequence that encodes an amino acid sequence of SEQ ID NO: 3, or an amino acid sequence having at least 95% sequence identity with the amino acid sequence of SEQ ID NO: 3, with a second *Brassica* plant that lacks the nucleic acid molecule to provide progeny *Brassica napus* plant; and
   selecting a *Brassica napus* progeny plant that tests positive for the presence of the nucleotide sequence.

3. The *Brassica napus* plant obtained by the method according to claim 1.

4. The *Brassica napus* plant according to claim 3, further comprising at least one other disease resistance gene, said other disease resistance gene is a clubroot resistance gene, a blackleg resistance gene, a *Sclerotinia* resistance gene, a *Verticillium* resistance gene, a *Fusarium* resistance gene, an Aster Yellows resistance gene, an *Alternaria* resistance gene, and/or a Grey Stem resistance gene.

5. Seeds grown on the *Brassica napus* plant of claim 3, wherein said seeds comprise a nucleic acid molecule comprising a nucleotide sequence that encodes an amino acid sequence of SEQ ID NO: 3, or an amino acid sequence having at least 95% sequence identity with the amino acid sequence of SEQ ID NO: 3.

6. Seeds according to claim 5 which are hybrid seeds.

7. The hybrid seeds of claim 6, which are *Brassica napus* hybrid seeds, and wherein said hybrid seeds develop into plants, the solid component of the seeds contains less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid.

* * * * *